US012733902B2

(12) United States Patent
Duckworth

(10) Patent No.: US 12,733,902 B2
(45) Date of Patent: Sep. 15, 2026

(54) SYSTEM FOR ACOUSTIC FETAL HEART RATE MONITORING

(71) Applicant: GE Precision Healthcare LLC, Waukesha, WI (US)

(72) Inventor: Kyle Duckworth, Lemont, IL (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 18/959,375

(22) Filed: Nov. 25, 2024

(65) Prior Publication Data

US 2026/0144515 A1 May 28, 2026

(51) Int. Cl.

| | |
|---|---|
| ***A61B 8/08*** | (2006.01) |
| ***A61B 8/00*** | (2006.01) |
| ***A61B 8/02*** | (2006.01) |
| ***G16H 40/67*** | (2018.01) |
| ***G16H 50/20*** | (2018.01) |

(52) U.S. Cl.

CPC .............. *A61B 8/0866* (2013.01); *A61B 8/02* (2013.01); *A61B 8/461* (2013.01); *A61B 8/488* (2013.01); *G16H 40/67* (2018.01); *G16H 50/20* (2018.01)

(58) Field of Classification Search

CPC ..... A61B 8/0866; A61B 8/02; A61B 5/02411; A61B 5/4343; G16H 50/20; G16H 80/00

See application file for complete search history.

(56) References Cited

U.S. PATENT DOCUMENTS

| | | | | |
|---|---|---|---|---|
| 8,821,415 | B2 | 9/2014 | Al-Ali et al. | |
| 9,370,335 | B2 | 6/2016 | Al-Ali et al. | |
| 9,717,412 | B2 | 8/2017 | Roham et al. | |
| 11,207,002 | B2 | 12/2021 | Khine et al. | |
| 2009/0216564 | A1* | 8/2009 | Rosenfeld ............. | A61B 5/411 705/2 |
| 2016/0354043 | A1* | 12/2016 | Heil ..................... | A61B 5/0011 |
| 2018/0317789 | A1 | 11/2018 | Ransbury et al. | |
| 2019/0388056 | A1* | 12/2019 | Rodriquez ........... | A61B 8/4236 |
| 2023/0170087 | A1* | 6/2023 | Holder .................. | G16H 50/20 705/2 |
| 2023/0309909 | A1* | 10/2023 | Holder ................ | A61B 5/6831 600/304 |

* cited by examiner

*Primary Examiner* — Carolyn A Pehlke

(74) *Attorney, Agent, or Firm* — McCoy Russell LLP

(57) ABSTRACT

Methods and systems are provided herein for a fetal heart rate (FHR) monitoring system that determines when to selectively record and transmit acoustic FHR as part of FHR data acquired via a patient monitor. Non-acoustic FHR data may be streamed to an analytics system that may analyze the non-acoustic FHR data to determine whether unexpected or anomalous patterns are present in the non-acoustic FHR data. When an unexpected or anomalous pattern is detected, the analytics system may send a request to the FHR monitoring system to record the acoustic FHR and bundle the recorded acoustic FHR with the non-acoustic FHR data using the Sapphire over Unified Messaging Fabric (sUMF) protocol, which supports audio streams. The FHR data including the acoustic FHR data may then be transmitted to a surveillance station for viewing by a clinician, who may be notified by the acoustics system of the unexpected or anomalous pattern.

19 Claims, 10 Drawing Sheets

SYSTEM FOR ACOUSTIC FETAL HEART RATE MONITORING

TECHNICAL FIELD

Embodiments of the subject matter disclosed herein relate to monitoring physiological signals of a patient, including fetal heart rate activity in a fetus of a pregnant mother.

BACKGROUND

Cardiotocography (CTG) is widely used in pregnancy as a method of assessing fetal well-being, particularly during labor and delivery. CTG records changes in the fetal heart rate (FHR) and their temporal relationship to uterine contractions. The machine used to perform the monitoring is called a cardiotocograph, more commonly known as an electronic fetal monitor (EFM). Simultaneous recordings are performed by two separate transducers, one for the measurement of the FHR and a second one for the uterine contractions, also referred to as the uterine activity (UA). The transducers may be either external or internal. The cardiograph recordings are typically in the form of graphical tracings that are either printed on a continuous strip of paper and/or displayed on a graphical display monitor.

The FHR and UA tracings are typically analyzed manually by an obstetric medical team (e.g., including nurses, resident physicians, nurse midwives, attending physicians, etc.) over the course of labor to identify abnormal patterns. The identification of the patterns helps in assessing various parameters and/or conditions associated with the fetus and/or the mother, such as baseline FHR, contraction duration and frequency, contraction nature (e.g., late, early, variably), FHR variability, and presence of tachysystole. Assessment of these parameters/conditions plays a significant role in identifying fetal abnormalities and assessing intervention during labor. Additionally or alternatively, the conditions associated with the fetus and/or mother may be identified by auscultation, where a clinician listens to the FHR via a listening device, such as a stethoscope or a Doppler transducer.

SUMMARY

The current disclosure at least partially addresses one or more of the above identified issues via a fetal monitoring system, comprising a fetal monitor including a processor and a non-transitory memory storing a set of instructions that when executed, cause the processor to continuously acquire fetal heart rate (FHR) data of a fetus of a pregnant mother from one or more sensors arranged on an abdomen of the pregnant mother; process the FHR data received using one or more artificial intelligence (AI) models; and in response to the one or more AI models detecting an anomaly in the FHR data: initiate recording of acoustic FHR data of the fetus via the one or more sensors; store the FHR data and the acoustic FHR data in a database; display a continuous graphical tracing of the FHR data of the fetus on a display device; and output the acoustic FHR data to a listening device.

The above advantages and other advantages, and features of the present description will be readily apparent from the Detailed Description below when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
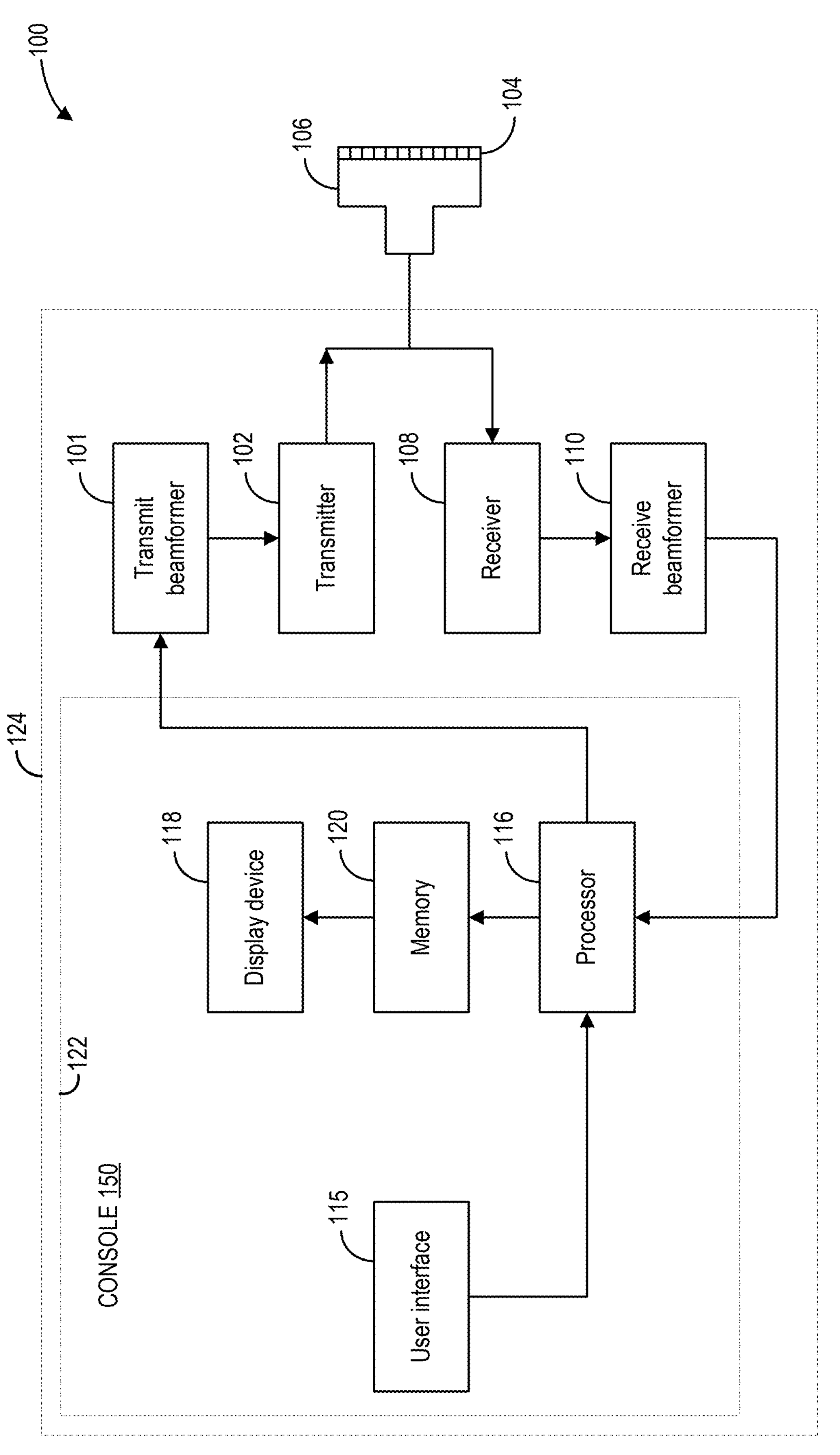
FIG. 1 shows a block diagram of an exemplary ultrasound system.

Accurately evaluating the well-being of a fetus during labor and delivery may lead to a healthy newborn and mother. Electronic Fetal Monitoring (EFM) is a common obstetrical procedure in the US, and most women undergo EFM during pregnancy, labor, and delivery. The rationale for use of EFM assumes that Fetal Heart Rate (FHR) abnormalities accurately reflect risk of hypoxia (inadequate low oxygenation of the fetus), and that early recognition of hypoxia could induce intervention to improve outcomes for the fetus. EFM may also be used to detect post-partum hemorrhage due to lack of contraction of uterus. EFM is often used to evaluate fetal well-being during the labor process by recording fetal heartbeat and frequency of uterine contractions via two monitors/transducers—an ultrasound device and a tocodynamometer (toco), respectively.

During labor, care providers may place an ultrasonic transducer of an electronic fetal monitor (EFM) over the mother's abdomen above the fetus, once detected, where a consistent fetal heartbeat may be detected. Ultrasonic gel may be applied between the transducer and a surface of the mother's abdominal skin. The transducer is held to the abdomen with a first elastic belt, wearable patch, or similar apparatus. The toco transducer may be applied to the abdomen above the umbilicus where the fundal height of the uterus is palpated, and may be held to the upper part of the abdomen by a second elastic belt. A heartbeat of the fetus may be detected in the ultrasound data during uterine contractions, while contraction detection via the toco allows monitoring of the progress of labor.

Cardiograph data acquired via the two separate transducers may be recorded. The recorded cardiograph data may be used to generate graphical tracings that are either printed on a continuous strip of paper and/or displayed on a graphical display monitor. The graphical tracings may be analyzed by an obstetric clinician over the course of labor to identify abnormal patterns to assess conditions associated with the fetus and/or the mother, such as baseline FHR, contraction duration and frequency, contraction nature (e.g., late, early, variably), FHR variability, and presence of tachysystole. The graphical tracings may be analyzed remotely, where the recorded cardiograph data may be digitized and streamed to a remote surveillance station over a network where the clinician may view the tracings on a remote display device. The clinician may review the tracings manually to determine whether the FHR exhibits anomalous behavior. In this way, fetal monitoring may be advantageously performed by clinicians that are not physically located at the patient. The fetal monitoring may also be performed, including simultaneously, by various clinicians at different locations, and/or at different times. As a result, a number of clinicians that are relied on to perform fetal monitoring may be reduced, and consultation between clinicians regarding patients may be increased, leading to faster identification of anomalous events concerning the fetus.

Additionally, the FHR may be analyzed by one or more artificial intelligence (AI)-based systems. The AI-based systems may include AI models that are trained to classify fetal heart rhythms into different categories, for example. The AI-based systems may include anomaly detection algorithms or models that take the FHR as input, and detect patterns in the FHR associated with anomalies. When an anomalous pattern is detected, an alert may be triggered. The alert may be seen or received by a clinician, who may review the FHR tracings to confirm the categorization or anomalous pattern. In various scenarios, the one or more AI-based systems may be hosted on a server in a cloud, where greater processing and memory resources may be available for training and running the one or more AI-based systems.

In some cases, the graphical tracings may be difficult to manually analyze, where the abnormal patterns may not be easily identified. In such cases, the conditions associated with the fetus and/or mother may be additionally or alternatively identified by auscultation, where the clinician listens to an acoustic FHR via a listening device, such as a stethoscope or a Doppler transducer. However, listening to the acoustic FHR is typically performed manually when the clinician is physically with the mother. That is, while an electronic stethoscope or Doppler transducer may be positioned on the abdomen of the mother, current technology may not support listening to the acoustic FHR remotely via a network, where a protocol used to stream numeric values comprising the recorded cardiograph data may not support transmission of audio files.

To address this problem, the inventors herein propose to transmit the FHR data using a protocol that provides a higher level of control over the types of data and formats that may be transmitted, and supports the inclusion of audio streams to transmit the recorded cardiograph data, such as the Sapphire over Unified Messaging Fabric (sUMF) protocol. Sapphire is a family of protocols based on a common data model for patients, healthcare devices, and the data they produce. The core data model is described in a set of XML documents. Each Sapphire compliant protocol includes a set of rules for encoding the data, and defines mechanisms used to transport Sapphire information. Sapphire has two unique features that make it especially relevant for healthcare data. First, the data model includes rich metadata about each observation, including units of measure and scale embedded in the protocol, so that applications can use the information at runtime. Second, as data model descriptions may be dynamically exchanged between Sapphire peers, this leads to enhanced interoperability. By using the sUMF protocol, the acoustic FHR can be recorded and streamed along with the FHR data used to generate the graphical tracings.

However, one problem with streaming acoustic FHR data is that the amount of data streamed may be large (e.g., significantly larger than the numeric FHR data). Because a number of obstetric patients may be high, and because a hospital network may have limited bandwidth, it may not be feasible to stream acoustic FHR data to remote caregivers continuously from a plurality of patients. Further, FHR data is typically stored in a memory of a UA, at least temporarily, as clinicians may not be able to monitor and review the FHR data of the plurality of patients simultaneously. While it is desirable to store FHR acoustic data, a size of audio files generated from the acoustic FHR streams may be prohibitively large.

To address this problem, systems and methods are provided herein for a FHR monitoring system that determines when to selectively record and transmit the acoustic FHR along with and/or as part of the FHR data, and when to transmit the FHR data without the acoustic FHR. Specifically, in accordance with the methods described herein, the non-acoustic FHR data may be streamed to an analytics system, which may be a cloud-based system. The analytics system may analyze the non-acoustic FHR data to determine whether unexpected or anomalous patterns are present in the non-acoustic FHR data. When an unexpected or anomalous pattern is detected, the analytics system may send a request to the FHR monitoring system to record the acoustic FHR and include the recorded acoustic FHR with the non-acoustic FHR data used to generate the graphical FHR tracings. The FHR data including the acoustic FHR data may then be transmitted to a surveillance station for viewing by a clinician, who may be notified by the acoustics system of the unexpected or anomalous pattern.

In this way, a size of the acoustic FHR data that is transmitted over the network and stored in the memory may be significantly reduced. By excluding acoustic FHR data that does not have unexpected or anomalous patterns from transmission and storage, it may be feasible for the acoustic FHR data to be transmitted and stored for later review without taxing available resources or bandwidth. As a result, clinicians including remote clinicians may access both the (traditional) graphical tracings and the acoustic FHR data from remote locations, which may lead to faster, more accurate, and more efficient diagnosis of fetal conditions.

Referring now to FIG. 1, a schematic diagram of an ultrasound system 100 in accordance with an embodiment of the disclosure is shown. The probe 106 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body of a patient (not shown). The probe 106 may be a one-dimensional transducer array probe, or may be a two-dimensional matrix transducer array probe. The transducer elements 104 may be comprised of a piezoelectric material, such as lead zirconate titanate (PZT), lead magnesium niobate-lead titanate (PMN-PT), single crystal PMN-PT (PIN-PMN-PT), or a different piezoelectric material. It should be appreciated that the examples provided herein are for illustrative purposes and a different type of piezoelectric material may be used without departing from the scope of this disclosure. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data to a processor 116 (e.g., also herein described as controller 116) to be displayed on a display device 118. Additionally, transducer element 104 may produce one or more ultrasonic pulses to form one or more transmit beams in accordance with the received echoes. The terms "scan" or "scanning" may also be used in this disclosure to refer to acquiring data through the process of transmitting and receiving ultrasonic signals.

Components of the ultrasound system 100 shown in FIG. 1 may be included in a console 150, or may be included in the probe 106, where the probe 106 may be electronically coupled to the console 150 via a cable. In some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106, where the console 150 may include the components depicted within dotted lines 122. In other embodiments, the console 150 may include the transmit beamformer 101, the transmitter 102, the receiver 108, and the receive beamformer 110, where the console 150 may include the components depicted within dashed lines 124. It should be appreciated that the ultrasound system 100 depicted in FIG. 1 is for illustrative purposes, and in other embodiments the ultrasound system 100 may include a greater or lesser number of components located either in the probe 106 or the console 150.

The console 150 may include a user interface 115, which may be used to control operation of the ultrasound system 100. The user interface 115 may include one or more of the following: a rotary element, a mouse, a keyboard, a trackball, hard keys linked to specific actions, soft keys that may be configured to control different functions, and/or a graphical user interface displayed on the display device 118.

The processor 116 may control the transmit beamformer 101. The processor 116 is in electronic communication (e.g., communicatively connected) with the probe 106. The term "electronic communication" may be defined to include both wired and wireless communications, although, for purposes of this disclosure, the probe 106 may be coupled to the console 150 via a first set of wires used to send a transmit signal to transmit beamformer 101, and a second set of wires used to receive a receive signal from receive beamformer 110 (e.g., the cable). The processor 116 may control the probe 106 to acquire data according to instructions stored on a memory 120.

As discussed herein, memory includes any non-transient computer readable medium in which programming instructions are stored. For the purposes of this disclosure, the term tangible computer readable medium is expressly defined to include any type of computer readable storage. The example methods and systems may be implemented using coded instruction (e.g., computer readable instructions) stored on a non-transient computer readable medium such as a flash memory, a read-only memory (ROM), a random-access memory (RAM), a cache, or any other storage media in which information is stored for any duration (e.g. for extended period time periods, permanently, brief instances, for temporarily buffering, and/or for caching of the information). Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include any other medium which can be used to store the desired electronic format of information and which can be accessed by the processor or processors or at least a portion of a computing device.

The processor 116 and the transmit beamformer 101 control which of the elements 104 are active and the shape of a beam emitted from the probe 106. The processor 116 is in electronic communication with the display device 118, and the processor 116 may process the data (e.g., ultrasound data) into physiological signals for display on the display device 118. The processor 116 may include a central processor (CPU) and/or graphic processing units (GPU), according to an embodiment. According to other embodiments, the processor 116 or transmit beamformer 101 may include other electronic components capable of carrying out processing functions, such as a microprocessor, a microcontroller, or a field-programmable gate array (FPGA). According to other embodiments, the processor 116 may include multiple electronic components capable of carrying out processing functions. For example, the processor 116 may include two or more electronic components selected from a list of electronic components including: a central processor, a digital signal processor, an FPGA, and a graphic board. According to another embodiment, the processor 116 may also include a complex demodulator (not shown) that demodulates the received signals and generates raw data. In another embodiment, the demodulation can be carried out earlier in the processing chain (e.g. receive beamformer 110).

The processor 116 may be adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire physiological signals at a real-time rate of 4-20 samples/sec. Some embodiments of the invention may include multiple processors (not shown) to handle the processing tasks that are handled by processor 116 according to the exemplary embodiment described hereinabove. For example, a first processor may be utilized to demodulate and decimate the received signals while a second processor may be used to further process the data, for example by augmenting the data as described further herein, prior to displaying a physiological signal. It should be appreciated that other embodiments may use a different arrangement of processors.

The ultrasound system 100 may continuously acquire data at a sample-rate of, for example, 4 Hz to 30 Hz (e.g., 10 to 30 frames per second). Physiological signals may be generated from the data may be refreshed at a similar sample-rate on display device 118. Other embodiments may acquire and display data at different rates. For example, some embodiments may acquire data at a sample-rate of less than 4 Hz or greater than 30 Hz depending on the size of the frame and the intended application. A memory 120 is included for storing processed frames of acquired data. In an exemplary embodiment, the memory 120 is of sufficient capacity to store at least several seconds'worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The received ultrasound signals are stored in memory and may include timing information indicating a time at which the physiological time-series signal samples were stored in memory. The modules may include, for example, a scan conversion module to perform scan conversion operations to convert the acquired physiological signals from beam space coordinates to display space coordinates. A video processor module may be provided that reads the acquired physiological signals from a memory and displays physiological signals in real time while a procedure (e.g., ultrasound imaging) is being performed on a patient. The video processor module may include a separate physiological signals memory, and the ultrasound physiological signals may be written to the physiological signals memory in order to be read and displayed by display device 118.

After performing an ultrasound scan, a block of data comprising scan lines and their samples is generated. After back-end filters are applied, a process known as scan conversion is performed to transform the data block into a displayable physiological signal with additional scan information such as depths, angles of each scan line, and so on. During scan conversion, an interpolation technique is applied to fill missing holes (e.g., samples) in the resulting physiological signals. These missing samples occur because each element of the transducers should typically cover many samples in the resulting signal.

In embodiments where the transmit beamformer 101 is included in the console 150 and not in the probe 106, the ultrasound system 100 may be configured to transmit a signal from transmit beamformer 101 to the probe 106 for operating the probe 106. In embodiments where the transmit beamformer 101 is included in the probe 106 and not in the console 150, the ultrasound system 100 may be configured to transmit beam setup data from the processor 116 (e.g., and/or from an FPGA of the processor 116) to transmit beamformer 101 for operating probe 106. The beam setup data may be transmitted as low voltage digital signals, as opposed to the high voltage transmit signal. A dedicated set of wires may be used for such purposes. However, a number of wires in the dedicated set of wires may be small (e.g., four), and an amount of beam setup data transmitted from the processor 116 may be large, which may cause delays in operating probe 106 due to slow data transfer rates.

In addition to generating physiological signals, an amplitude of the reflected receive signal may also be recorded over predefined increments of time to generate time-series data. In particular, during transabdominal ultrasound procedures performed on pregnant mothers as part of electronic fetal monitoring, the time-series data may be used to detect a heartbeat of a fetus of a pregnant mother, or to monitor uterine activity before, during, or after labor. The time-series data may be used to generate a graphical tracing of the heartbeat of the fetus that may be displayed on a display device, either locally at the patient or remotely via a network.

Figure 2:
FIG. 2 shows an exemplary UA.
Figure 2:
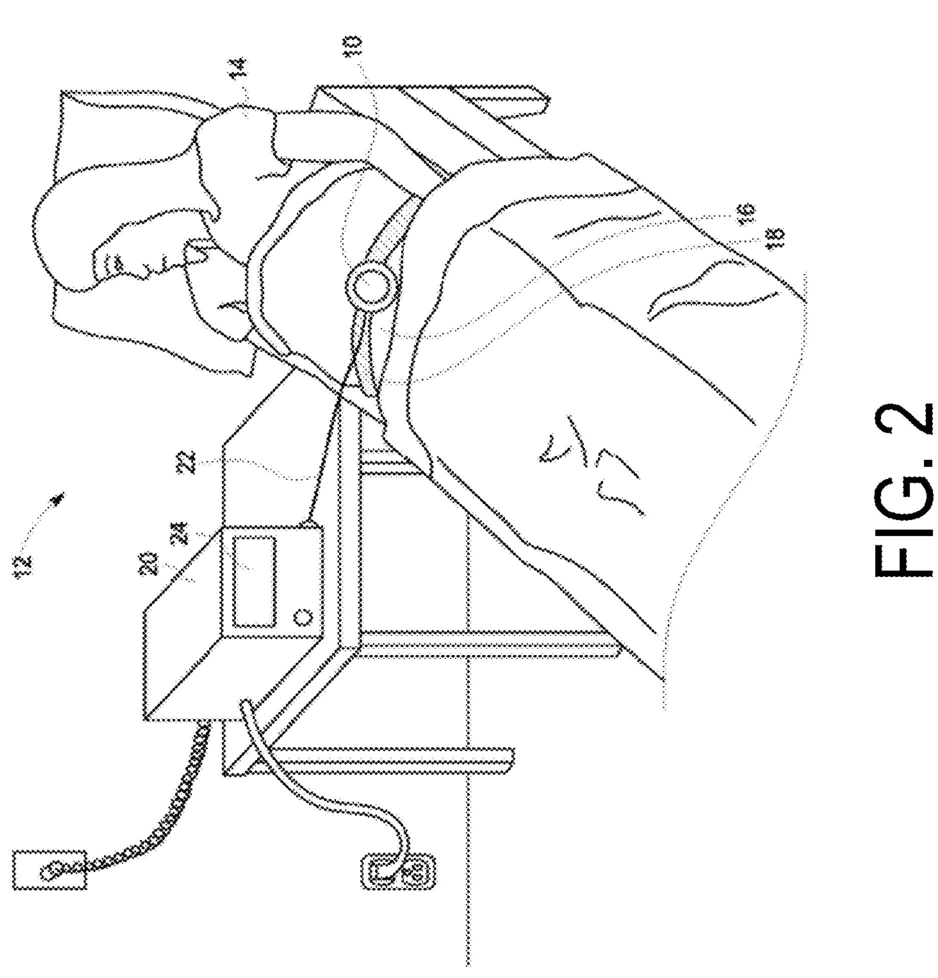

FIG. 2 is an environmental view 200 of an exemplary embodiment of a maternal and fetal monitoring system 12. Fetal monitoring system 12 includes use of an ultrasound transducer 10, which may be used for simultaneously monitoring the health of a maternal patient and fetal patient. Ultrasound transducer 10 is exemplarily secured to the abdomen 16 of the maternal patient 14, for example, by way of an elastomeric strap 18. However, it will be recognized that in other embodiments, a biocompatible adhesive may be used to secure the ultrasound transducer 10 to the patient's abdomen 16.

The ultrasound transducer 10 may be communicatively connected to a monitoring device 20 by a communicative connection 22, which may be a wired or a wireless communicative connection. Depending upon the configuration of the maternal and UA and the data transmitted between the ultrasound transducer 10 and the monitoring device 20, some or all of the data processing of the physiological information acquired by the ultrasound transducer 10 may be performed locally at the ultrasound transducer 10. A controller located within the ultrasound transducer 10 may receive the acquired physiological data and process such physiological data in the manners as described herein and the calculated parameters of fetal heart rate (HR), maternal HR, UA or others as described herein may be communicated across the communicative connection 22 to the monitoring device 20 exemplarily for visual presentation on a graphical display 24 and/or electronic storage of this information on a data network of the hospital or medical facility and exemplarily in a electronic medical record (EMR) of the maternal patient.

In other embodiments, the ultrasound transducer 10 may perform more limited signal processing on the acquired physiological data and provide this physiological data across the communicative connection 22 to a monitoring device 20 which applies the signal processing actions and techniques as described herein to calculate the parameters of fetal HR, maternal HR, UA, and others.

The ultrasound transducer 10 includes an ultrasound interface constructed of an acoustically conductive material. In use, an acoustic enhancing substance which may be a liquid, paste, gel, or solid material may be interspersed between the ultrasound interface and the abdomen 16 of the maternal patient. Additionally, a tocodynameter may be positioned on the abdomen of the mother, which may measure ultrasound contractions. The toco may include a plurality of electrodes arranged in a housing on a patient side of the toco surrounding a second ultrasound interface. The electrodes may be configured to interface with the skin of the maternal patient to acquire electric biopotentials including biopotential components from the maternal heart, a fetal heart, and other biopotential sources, including electromyographical (EMG) signals from the maternal and/or fetal patient.

Figure 3:
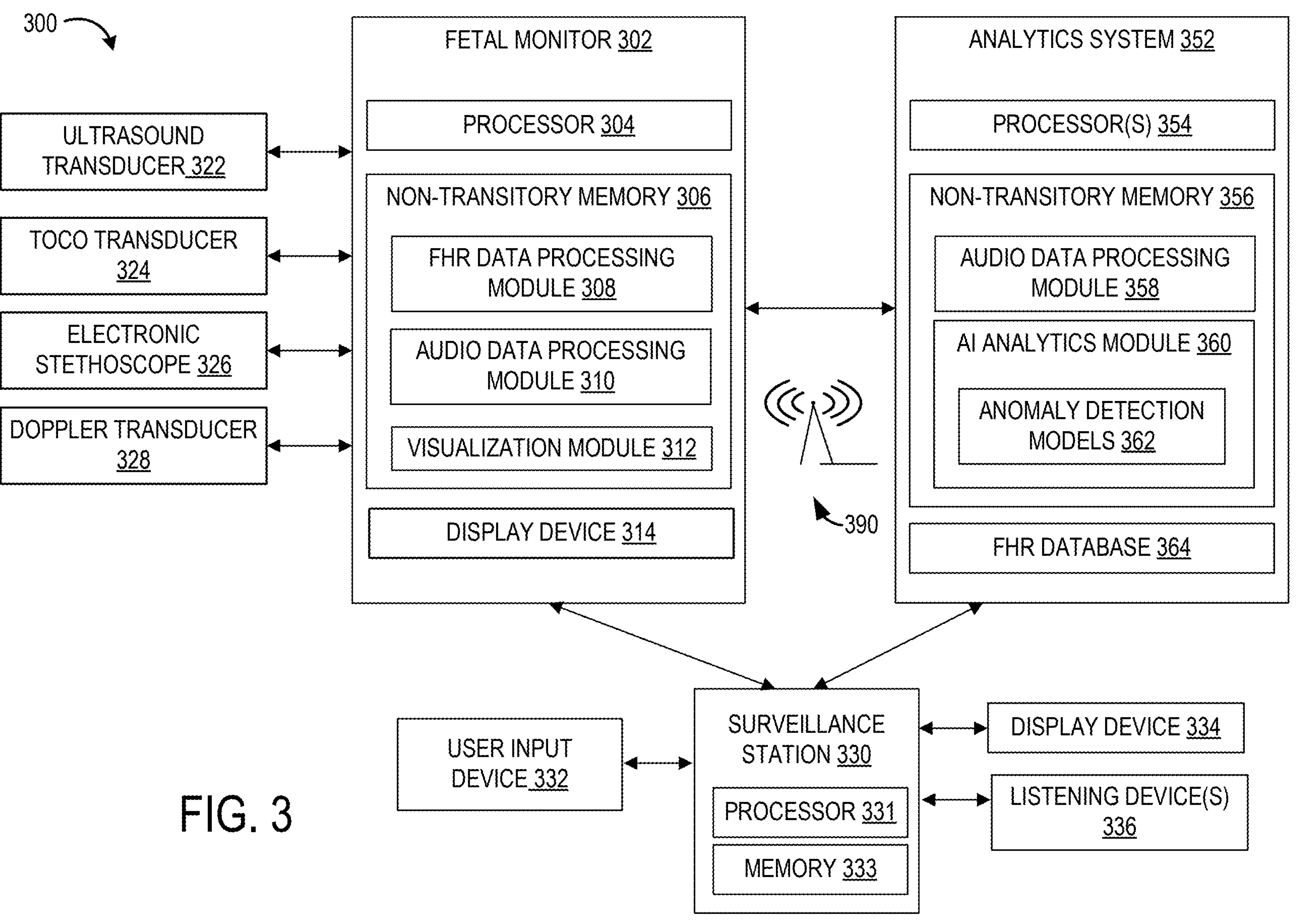
FIG. 3 is a schematic diagram of exemplary local and cloud-based UAs.

Referring now to FIG. 3, a schematic diagram of an exemplary fetal monitoring system 300 is shown, in accordance with an embodiment. Fetal monitoring system 300 includes a fetal monitor 302, which may be a non-limiting example of fetal monitoring system 12 of FIG. 2. Fetal monitor 302 may monitor an FHR of a fetus of a pregnant mother. Fetal monitor 302 may also monitor uterine activity and/or other physiological data of the pregnant mother and/or fetus.

Fetal monitor 302 may be communicably coupled to an ultrasound transducer 322 (e.g., of ultrasound system 100), a toco transducer 324, an electronic stethoscope 326, and/or a Doppler transducer 328, via wired and/or wireless connections. Fetal monitor 302 may receive physiological time-series data of a pregnant mother and a fetus of the pregnant mother from ultrasound transducer 322 and toco transducer 324. Fetal monitor 302 may receive acoustic FHR data from electronic stethoscope 326 (e.g., a fetoscope) and/or Doppler transducer 328.

Fetal monitor 302 includes a processor 304 configured to execute machine readable instructions stored in a non-transitory memory 306. Processor 304 may be single core or multi-core, and the programs executed thereon may be configured for parallel or distributed processing. In some embodiments, processor 304 may optionally include individual components that are distributed throughout two or more devices, which may be remotely located and/or configured for coordinated processing. In some embodiments, one or more aspects of processor 304 may be virtualized and executed by remotely-accessible networked computing devices configured in a cloud computing configuration.

Non-transitory memory 306 may store an FHR data processing module 308, an audio data processing module 310, and a visualization module 312. FHR data processing module 308 may include instructions for performing processing on FHR data acquired via ultrasound transducer 322 and/or toco transducer 324 prior to being transmitted to a clinician for review. The processing of the FHR data may include encoding the FHR data in accordance with a protocol for transmitting the FHR data to the clinician, such as the sUMF protocol described above.

Audio data processing module 310 may include instructions for processing acoustic FHR data acquired via electronic stethoscope 326 and/or Doppler transducer 328. The processing of the acoustic FHR data may include converting the acoustic FHR data to an audio stream to be transmitted to the clinician in accordance with the UMF protocol. In particular, FHR data processing module 308 and/or audio data processing module 310 may include instructions that when executed by processor 304, may perform one or more steps of method 500 of FIG. 5 described below.

Visualization module 312 may include instructions for visualizing the FHR data on a display device 314 of fetal monitor 302, such as FHR data acquired via ultrasound transducer 322 and/or toco transducer 324. Visualizing the FHR data may include generating a graphical tracing of the FHR data and/or other displaying other elements or aspects of the FHR data on display device 314 of fetal monitor 302.

Fetal monitor 302 may be communicatively coupled to an analytics system 352 and one or more surveillance stations 330 via a network 390. Network 390 may be a wireless network, and may include the Internet. As described in greater detail herein, fetal monitor 302 may transmit the acquired FHR data (including acoustic FHR data) to analytics system 352 for additional processing. In various embodiments, analytics system 352 may be a cloud-based fetal analytics system that avails of greater processing and memory resources than fetal monitor 302. Fetal monitor 302 may also transmit the acquired FHR data (including acoustic FHR data) to the one or more surveillance stations 330, where the FHR data and/or acoustic FHR data may be viewed or listened to by a clinician.

Analytics system 352 includes one or more processors 354 and a non-transitory memory 356 storing instructions that when executed by processor 354, may perform one or more steps of methods 600 and 700 of FIGS. 6 and 7 described below, respectively. Non-transitory memory 356 includes an audio data processing module 358, which may be used to process acoustic FHR data received from fetal monitor 302.

Non-transitory memory 356 may include an AI analytics module 360, which may take FHR data received from fetal monitor 302 as input. AI analytics module 360 may include various AI, machine learning (ML), and/or deep learning (DL) models of various types, including trained and/or untrained neural networks such as Convolutional Neural Networks (CNNs), statistical models, or other models, and may further include various data, or metadata pertaining to the one or more models stored therein. In some examples, an AI model of AI analytics module 360 may classify the received FHR data into one or more categories, or perform various statistical or pattern-matching analyses of the FHR data. AI analytics module 360 may additionally store instructions for implementing the one or more ML models.

In particular, AI analytics module 360 may include one or more anomaly detection models 362 known in the art, which may detect anomalous patterns in FHR data received from fetal monitor 302. When an anomalous pattern is detected, analytics system 352 may send an alert or notification to an appropriate clinician or surveillance station 330 for further review and/or diagnosis.

Analytics system 352 further includes an FHR database 364. FHR database 364 may store FHR data received from fetal monitor 302, including acoustic FHR data.

Analytics system 352 may be communicatively coupled to the one or more surveillance stations 330, where one or more clinicians may view and review FHR data acquired by fetal monitor 302 and/or analyzed at analytics system 352 and transmitted to the one or more surveillance stations 330 from cloud-based analytics system 352. Surveillance stations 330 may include a computing device including a processor 331 and a memory 333 that is operably/communicatively coupled to a user input device 332, a display device 314, and/or one or more listening devices 336 (e.g., speakers, headphones, etc.).

Each surveillance station 330 may be used by one or more clinicians. That is, a plurality of clinicians at a single surveillance station 330 may listen to acoustic FHR data of a single patient, or a plurality of patients, via one or more listening devices 336, or the plurality of clinicians may listen to the acoustic FHR data of the single patient or plurality of patients on a listening device 336 of a different surveillance station 330.

Display device 314 may include one or more display devices utilizing virtually any type of technology. In some embodiments, display device 314 may comprise a computer monitor. Display device 314 may be combined with surveillance station 330 and/or user input device 332 in a shared enclosure, or may be peripheral display devices and may comprise a monitor, touchscreen, projector, or other display device known in the art. The FHR data acquired by fetal monitor 302 may be displayed on display device 314, and acoustic FHR data acquired by fetal monitor 302 may be listened to by one or more clinicians via listening devices 336. User input device 332 may comprise one or more of a touchscreen, a keyboard, a mouse, a trackpad, or other device configured to enable a user to interact with and manipulate data transmitted to surveillance station 330.

It should be understood that fetal monitor 302 shown in FIG. 3 is for illustration, not for limitation. Another appropriate fetal monitoring system may include more, fewer, or different components.

Figure 4:
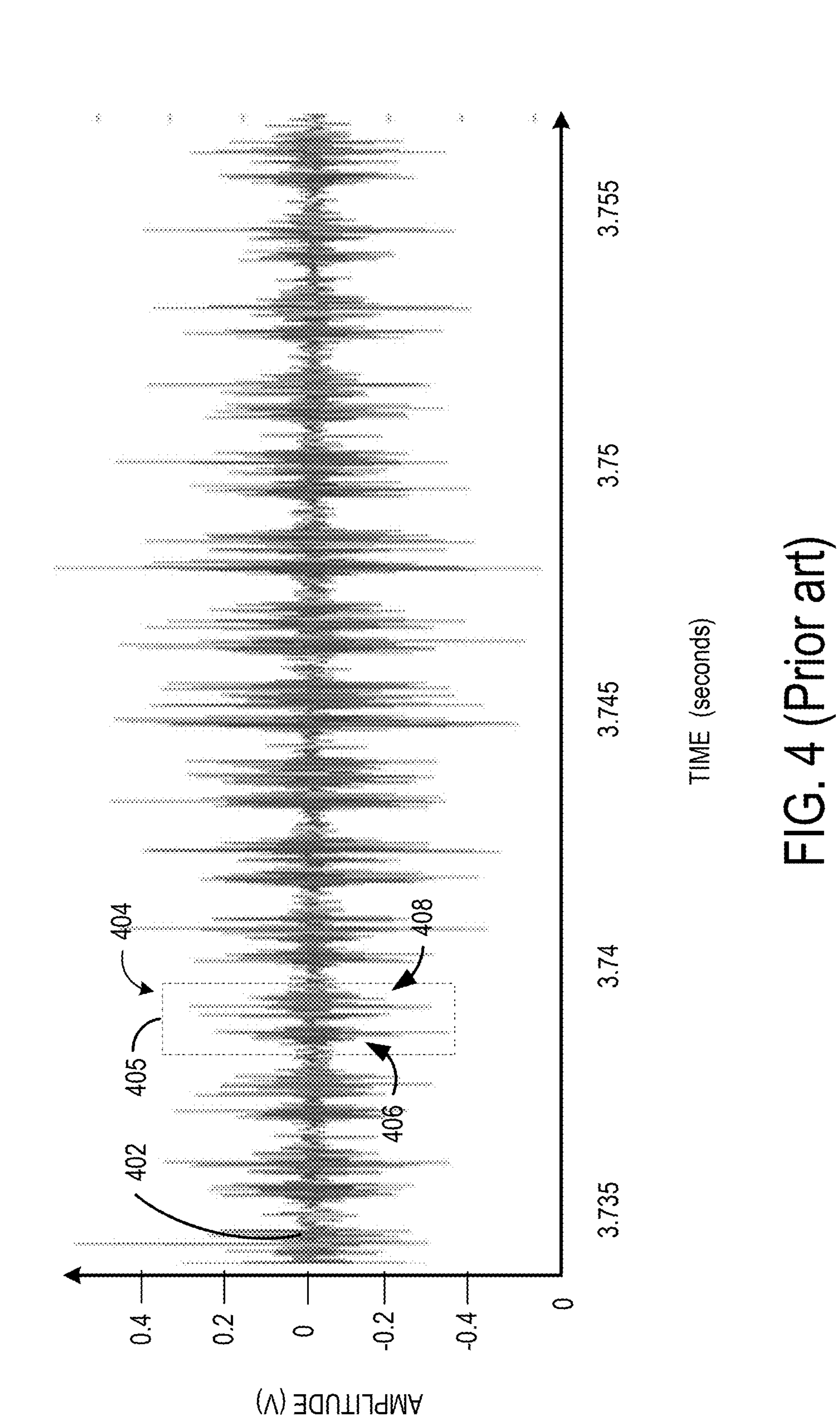
FIG. 4 shows an exemplary trace of a fetal heart rate (HR) generated from ultrasound data, as prior art.

FIG. 4 shows an exemplary time-series graph 400 of ultrasound data of a heartbeat of a fetus of a pregnant mother as a transabdominal ultrasound scan is being performed using an ultrasound system, such as ultrasound system 100 of FIG. 1. Uterine muscle contractions measurements recorded are reflected in raw ultrasound data acquired using an ultrasound transducer are indicated on a vertical axis of time-series graph 400 in mmHg, and time is indicated on a horizontal axis of time-series graph 400 in minutes.

Time-series graph 400 shows various fetal heartbeats 404, which are represented in an ultrasound plot 402. Ultrasound plot 402 may be generated by an ultrasound transducer placed or worn on an abdomen of the mother. Heart activity is characterized by two distinct periods called systole and diastole. During systole, the heart muscle is contracting the volume of the left ventricle to pump the contents out through the aortic valve. At the end of the systole, the left ventricle has its smallest volume since it has been contracted to pump blood out. During the diastole, or the diastolic period, the left ventricle is filling through the mitral valve. The end of the diastole is the point at which the left ventricle has its largest volume since it is filled with blood ready to be pumped out. Ultrasound fetal heart rate is detected as what is known as Lub-Dub pattern, where fetal heartbeat 404 includes a Lub portion 406 and a Dub portion 408. The Lub-Dub patterns may be processed for detection of a signal envelope 405.

Figure 5:
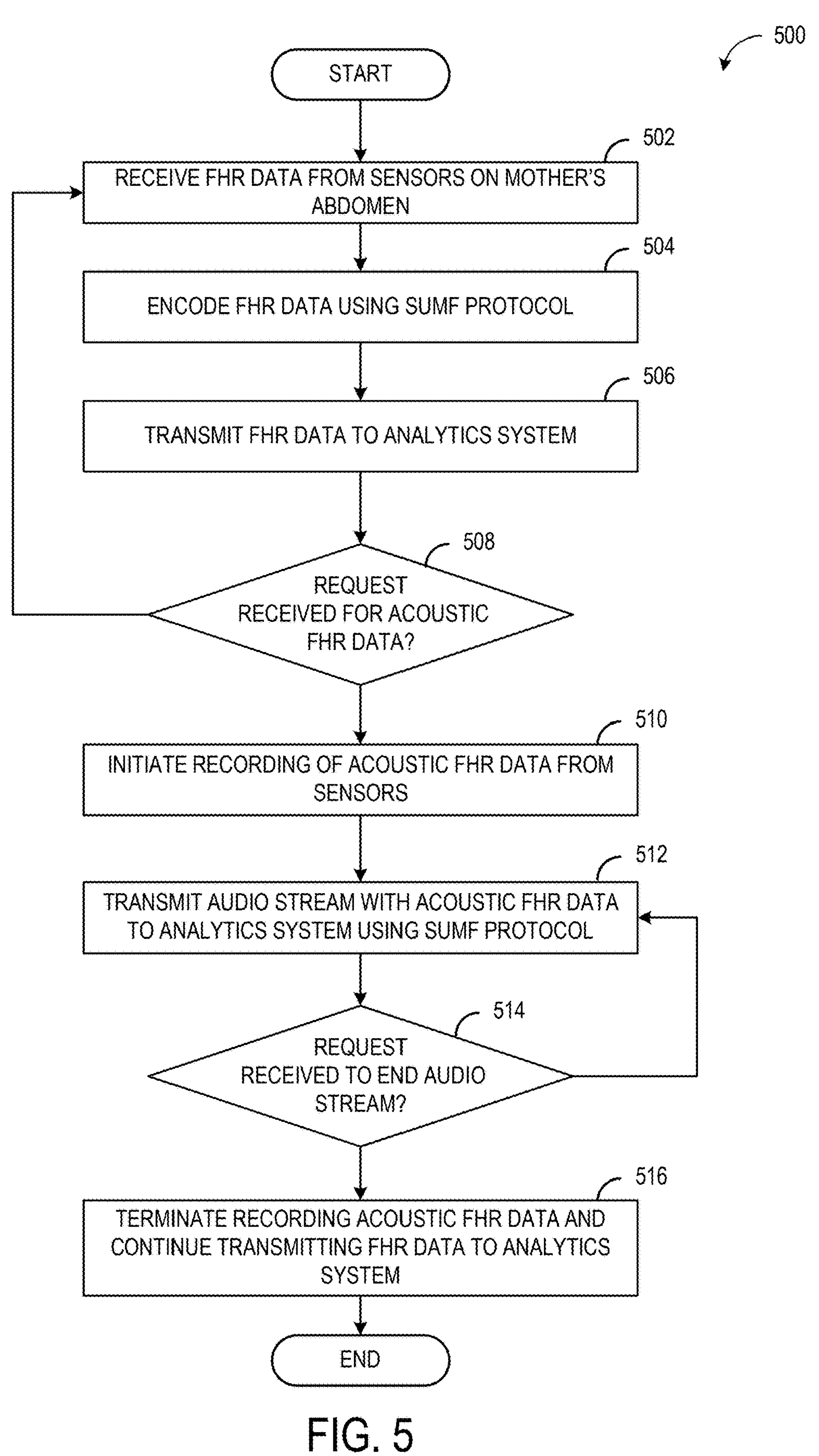
FIG. 5 is a flowchart illustrating an exemplary method for transmitting fetal HR data optionally including an acoustic fetal HR to the cloud-based UA.

Referring now to FIG. 5, an exemplary method 500 is shown for acquiring FHR data from a fetal monitoring system of a hospital, such as fetal monitoring system 300 of FIG. 3. Under conditions described herein, the FHR data may include acoustic FHR data acquired via an electronic stethoscope (e.g., electronic stethoscope 326) and/or a Doppler transducer (e.g., Doppler transducer 328), or a different acoustic device configured to acquire acoustic FHR data. Method 500 may be performed by a processor of a fetal monitor of the fetal monitoring system, such as fetal monitor 302 of FIG. 3. Operations of method 500 may be stored in non-transitory memory of the fetal monitor and executed by a processor of the fetal monitor (e.g., processor 304).

Method 500 begins at 502, where method 500 includes receiving FHR data from one or more sensors arranged on an abdomen of a pregnant mother. The received FHR data may be non-acoustic FHR data acquired via one or both of an ultrasound transducer (e.g., ultrasound transducer 322) and a toco transducer (e.g., toco transducer 324) communicatively coupled to the fetal monitor. The FHR data may be acquired continuously in real time. In some embodiments, the FHR data may be processed, for example, at FHR data processing module 308. For example, averaging and/or other statistical calculations may be performed on the acquired FHR data, in some examples.

At 504, method 500 includes encoding the FHR data into a protocol for transmitting the FHR data over a network (e.g., network 390). The protocol may be selected based on characteristics such as the ability to include rich metadata on clinical observations including units of measure and scale that are embedded in the protocol. In various embodiments, the selected protocol may be the sUMF protocol. sUMF is a set of software libraries, communication services, and the name of a distributed network protocol. This communication platform is built upon the Object Management Group (OMG) Distributed Data Service standard. While the overall hierarchy of data is canonical within all Sapphire encodings, the specification on the Sapphire UMF encoding is significantly different from the other Sapphire encodings.

Figure 10:
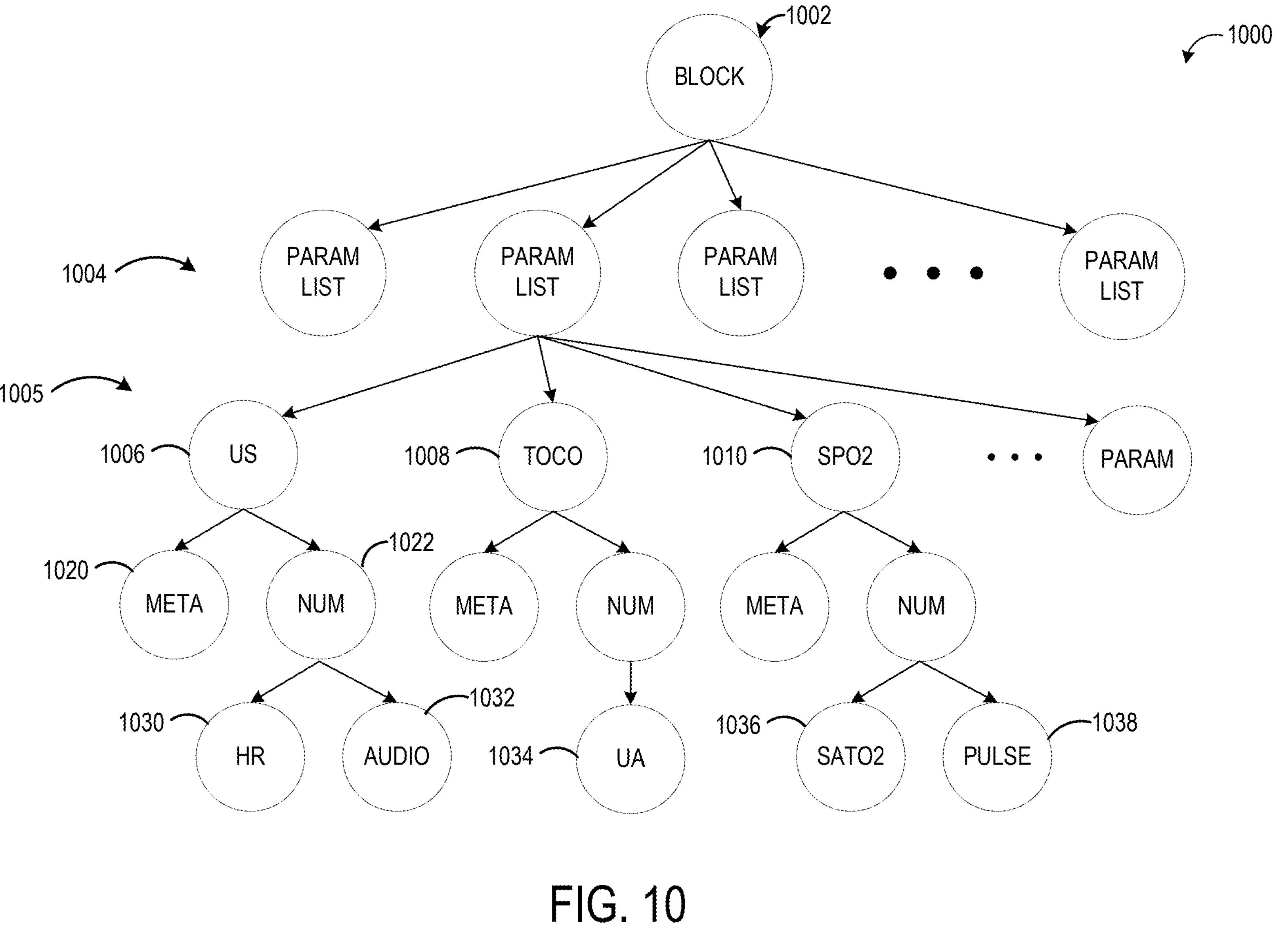
FIG. 10 is a schematic diagram of an exemplary encoding of data using the sUMF protocol.

Referring briefly to FIG. 10, a schematic diagram 1000 shows a hierarchical structure of the sUMF protocol, which may have characteristics that are advantageous for transmitting the FHR data, and in particular the acoustic FHR data over a network. The sUMF protocol encodes data as a series of blocks 1002, where each block 1002 includes a plurality of parameter lists 1004. Each parameter list 1004 may include a plurality of parameters 1005, which may correspond to a plurality of data sources. In the depicted example, parameters 1005 includes at least an ultrasound parameter 1006, a toco parameter 1008, and an SP02 parameter 1010. In other examples, more or different parameters 1005 may be included.

Each parameter 1005 (e.g., each data source) includes at least metadata 1020 associated with the parameter 1005 and numeric data 1022 acquired via the data source. Metadata 1020 may include, for example, serial numbers, labels, quality context, etc. For example, metadata 1020 of ultrasound parameter 1006 may include an FHR label; metadata 1020 of SPO2 parameter 1010 may include a site of acquisition; and so on.

Numeric data 1022 may comprise byte array data sets. Various numeric data 1022 may be defined for each parameter. In the depicted example, numeric data 1022 of the ultrasound parameter 1006 includes at least HR data 1030 and an audio stream 1032. For the ultrasound parameter, numeric values may be generated every 250 ms and may be sent every second in an array of four data point, e.g., [140, 139, 137, 140]. Audio stream 1032 may include the acoustic FHR data. Numeric data 1022 of the toco parameter 1008 may include UA data. Numeric data 1022 of the SPO2 parameter 1010 may include oxygen saturation data 1036 and pulse rate data 1038, for example.

The sUMF protocol has several advantages over a conventional serial protocol currently used, due to its flexibility. The conventional protocol may include a finite number of data codes that are supported, like fetal heart rate, device metadata, vitals, notes, alarms, etc. These messages may be denoted by a specific ASCII code within the message that the consuming digital solutions need to interpret and process accordingly. By adopting a dynamic and flexible protocol like sUMF, new data can be dynamically added to a message payload, with multiple messages combined into one payload, and a greater level of control over the sampling rate. The type of numeric data that are transmitted can be dynamically grown. In particular, two byte arrays can be enabled when requested: a first byte array including numeric data captured by a device, and a second byte array including a digitized byte representation of audio data. The conventional protocol may demand that data packets be acquired at specific times (e.g., every 250 ms, for example) and may aggregate multiple datapoints into one fetal heart rate data packet. A limitation on triplet support may also be removed, as the sUMF protocol can add parameters dynamically. The sUMF protocol also supports bi-directional capabilities; by using a flexible protocol like sUMF, a digital solution may be used in a command-control model with a fetal monitor, where the start, end, and type of data collected and transmitted by our devices can be managed.

Returning to method 500, at 506, method 500 includes transmitting the FHR data to an analytics system communicatively coupled to the fetal monitor (e.g., analytics system 352). In various embodiments, the analytics system is a cloud-based analytics system accessed via a network of the hospital. The cloud-based analytics system may have more computational and memory resources for analyzing and processing the FHR data than are available at the fetal monitor. For example, the cloud-based analytics system may input the received FHR data into one or more AI models trained in the cloud to detect anomalous behavior in the FHR of the fetus, as described below in reference to FIG. 6.

At 508, method 500 includes determining whether a request is received from the analytics system for acoustic FHR data. If at 508 no request is received, method 500 proceeds back to 502, and the FHR data is continued to be received from the sensors. If at 508 a request for the acoustic FHR data is received, method 500 proceeds to 510.

At 510, method 500 includes initiating recording of the acoustic FHR data via the one or more sensors. The acoustic FHR data may be recorded via one or both of a stethoscope (e.g., electronic stethoscope 326) and a Doppler transducer (e.g., Doppler transducer 328), or a different acoustic sensor.

At 512, method 500 includes transmitting an audio stream of the acoustic FHR data to the analytics system, using the sUMF protocol. In some examples, some preprocessing may be performed on the acoustic FHR data prior to transmission to the analytics system. For example, a format of the acoustic FHR data may be converted for generating the audio stream, parameters of the acoustic FHR data such as sampling rates may be changed, etc.

At 514, method 500 includes determining whether a request is received from the analytics system to terminate recording the acoustic FHR data. If at 514 no request is received, method 500 proceeds back to 512, and the acoustic FHR data is continued to be recorded from the sensors and transmitted to the analytics system. Alternatively, if at 514 a request to terminate recording the acoustic FHR data is received, method 500 proceeds to 516.

At 516, method 500 includes terminating recording the acoustic FHR data via the one or more sensors. The FHR data acquired via the ultrasound transducer and/or the toco may continue to be transmitted to the analytics system for analysis. Method 500 ends.

Figure 6:
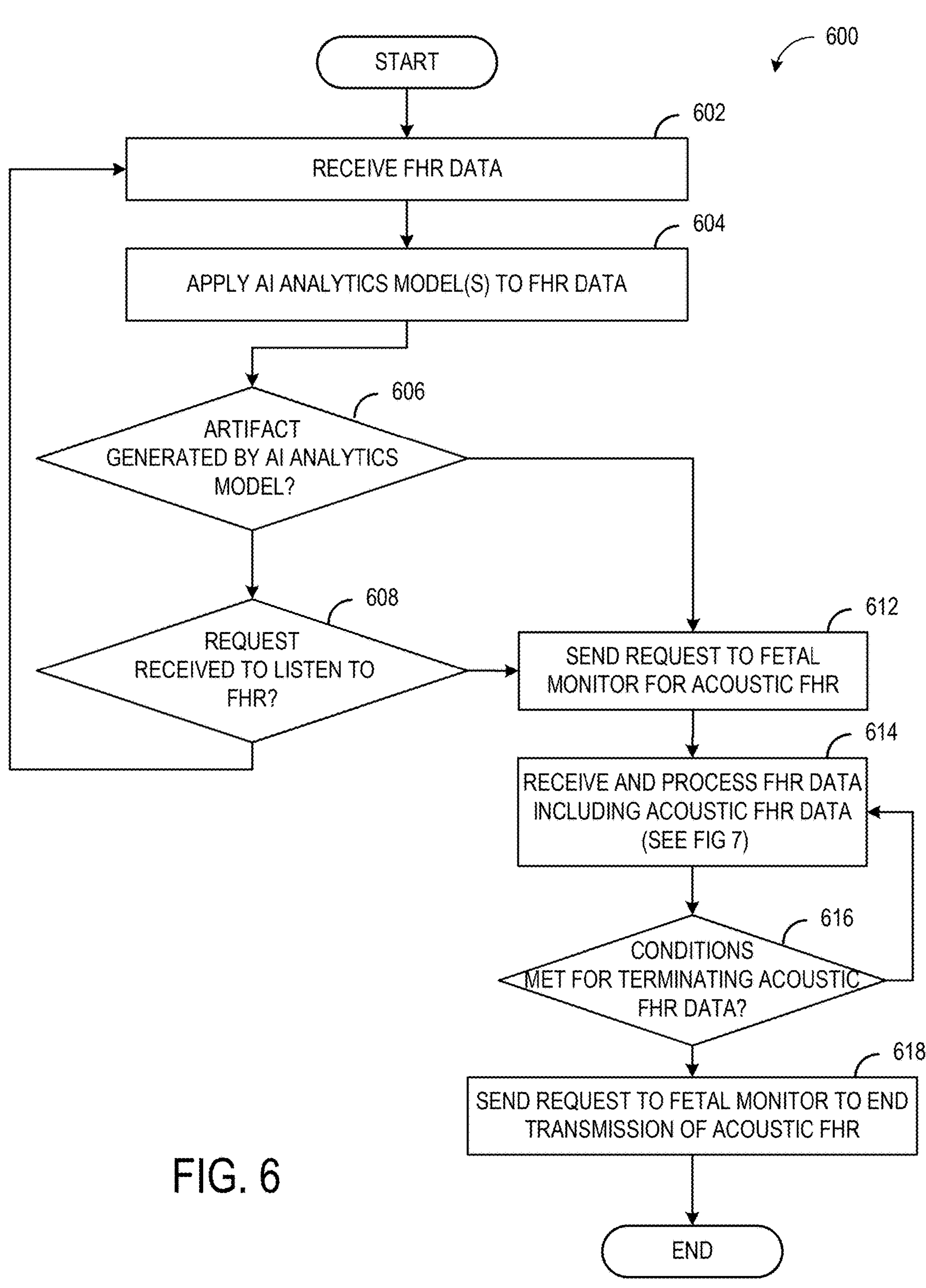
FIG. 6 is a flowchart illustrating an exemplary method for processing the fetal HR data at the cloud-based UA.

Referring now to FIG. 6, an exemplary method 600 is shown for analyzing FHR data received from a fetal monitor monitoring a fetus and a pregnant mother within a fetal monitoring system, such as fetal monitoring system 300 of FIG. 3. Method 600 may be performed by a processor of an analytics system of the fetal monitoring system, such as analytics system 352 of FIG. 3. Operations of method 600 may be stored in non-transitory memory of the analytics system (e.g., AI analytics module 360) and executed by a processor of the analytics system (e.g., processor 354). Method 600 may be performed in conjunction with method 500 of FIG. 5.

Method 600 begins at 602, where method 600 includes receiving FHR data from the fetal monitor. The FHR data may be acquired as described above in reference to FIG. 5. The FHR data may be received in a data stream encoded using the sUMF protocol, and receiving the FHR data may include extracting elements of the FHR data from the data stream.

At 604, method 600 includes applying one or more AI analytics models to the FHR data. The one or more AI analytics models may include classification models used to categorize the FHR data into one or more categories. In particular, the one or more AI analytics models may include anomaly detection models used to detect anomalies in the FHR data. Anomalies in the FHR data may indicate or be used to diagnose a condition of the fetus. For example, detected anomalies may include in increase in variability in the FHR; an acceleration or deceleration of the FHR; baseline changes of the FHR; or a detection of a sinusoidal pattern in the FHR or absent baseline variability plus recurrent late decelerations, recurrent variable decelerations, or bradycardia in the FHR (e.g., a National Institute of Child Health and Human Development (NICHD) category III state). The above examples of anomalies are not mutually exclusive or prescribed, and in various examples, the types of anomalies that are detected by the anomaly detection models may differ and may be configured by a user of the fetal monitoring system.

At 606, method 600 includes determining whether an artifact has been generated by an AI analytics model of the one or more AI analytics models. In one example, the artifact may be an anomaly detected in the FHR data by an anomaly detection model (e.g., anomaly detection model 362). If at 606 an artifact is generated, method 600 proceeds to 612.

At 612, method 600 includes sending a request to the fetal monitor for acoustic FHR data. The acoustic FHR data may be acquired as described above in reference to method 500.

At 614, method 600 includes receiving and processing the received FHR data including the acoustic FHR data. Processing the received FHR data including the acoustic FHR data is described below in reference to FIG. 7.

Returning to step 606, if at 606 an artifact is not generated, method 600 proceeds to 608. At 608, method 600 includes determining whether a request is received to output the acoustic FHR data to a listening device. In one example, the request may be received from a clinician (e.g., a caregiver of the pregnant mother), via a device such as a smart phone of the clinician or a surveillance station of the clinician. In another example, the request may be generated by a message sent from an EMR or third party system of a relevant health care system.

If at 608 no request is received, method 600 proceeds back to 602, where method 600 includes continuing to receive the FHR data. Alternatively, if at 608 a request to listen to the acoustic FHR data is received, method 600 proceeds to 612, where the acoustic FHR data is requested from the fetal monitor.

At 616, method 600 includes determining whether conditions have been met for terminating the recording and transmitting of the acoustic FHR data. The conditions for terminating the recording and transmitting of the acoustic FHR data may include not detecting anomalies in the non-acoustic FHR data. For example, an anomaly may be detected in the non-acoustic FHR data at a first time, and in response to detecting the anomaly, the analytics system may request acoustic FHR data from the fetal monitor. However, at a second, later time, the one or more AI analytics models may not detect the anomaly. For example, the anomaly may not represent a recurring or persisting condition. In such cases, conditions may be met for terminating the acoustic FHR data.

The conditions for terminating the recording and transmitting of the acoustic FHR data may also include receiving a request from a clinician (e.g., a caregiver of the pregnant mother) to terminate the recording and transmitting of the acoustic FHR data. For example, the acoustic FHR data may be transmitted to the clinician, as described below in reference to FIG. 7. The clinician may review the anomalous FHR data on a display device and may listen to the acoustic FHR data on a listening device. After reviewing the FHR data and/or listening to the acoustic FHR data, the clinician may form a diagnosis, and may have no further need for acoustic FHR data recorded after making the diagnosis.

If at 616 it is determined that conditions have been met for terminating the recording and transmitting of the acoustic FHR data, method 600 proceeds to 618. At 618, method 600 includes sending a request to the fetal monitor to terminate recording of the acoustic FHR at the fetal monitor and transmitting the acoustic FHR to the analytics system. Method 600 ends.

Figure 7:
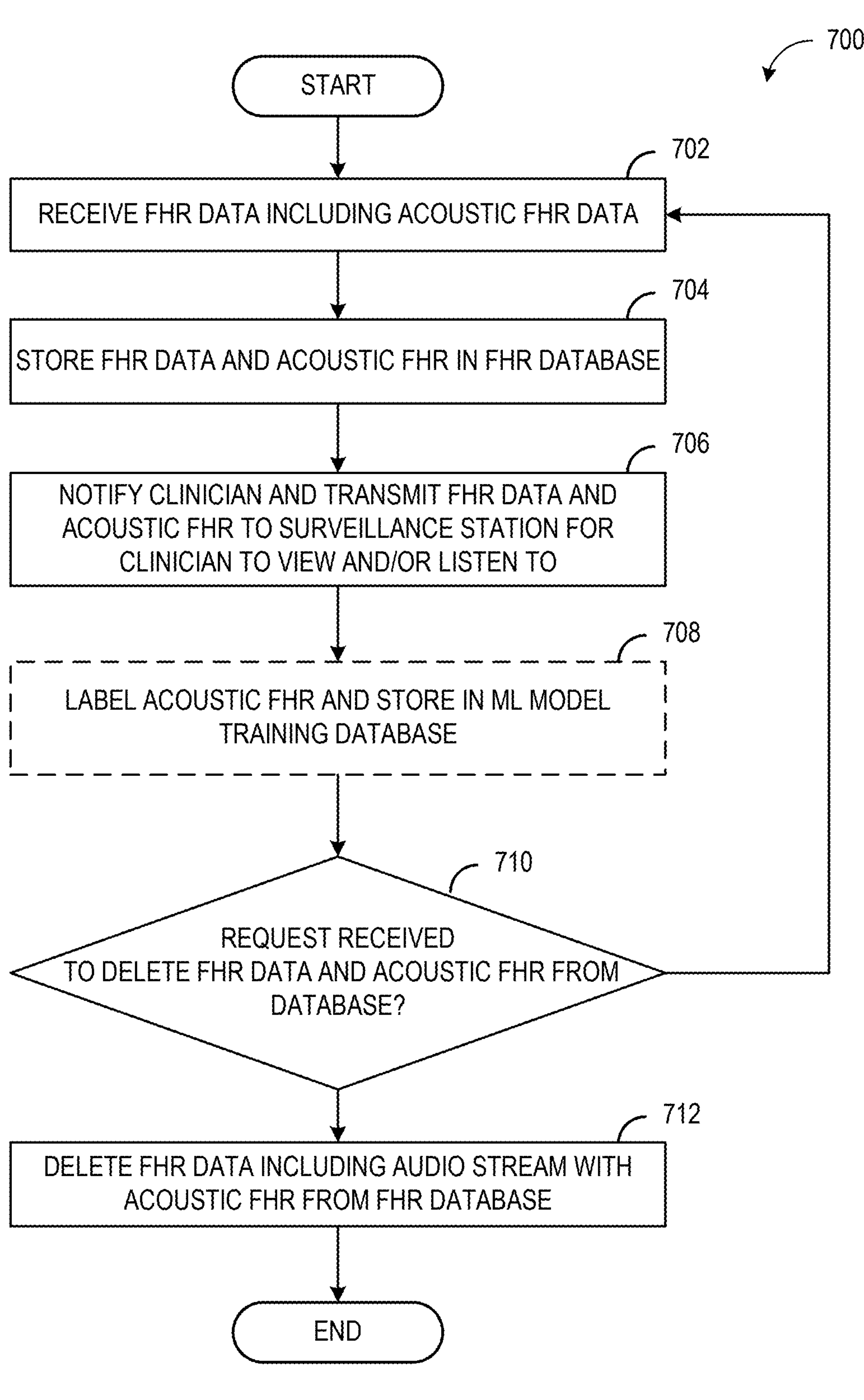
FIG. 7 is a flowchart illustrating an exemplary method for transmitting the fetal HR data including the acoustic fetal HR from the cloud-based UA to a surveillance station.

Referring now to FIG. 7, an exemplary method 700 is shown for processing FHR data received from a fetal monitor such as fetal monitor 302 and analyzed by one or more AI analytical models, as described in reference to method 600 of FIG. 6. Method 700 may be performed by a processor of an analytics system of the fetal monitoring system, such as analytics system 352 of FIG. 3. Operations of method 700 may be stored in non-transitory memory of the analytics system (e.g., non-transitory memory 356) and executed by a processor of the analytics system (e.g., processor 354). Method 700 may be performed as part of method 600 of FIG. 6.

Method 700 begins at 702, where method 700 includes receiving FHR data including acoustic FHR data. The FHR data may be received from the fetal monitor as described above in reference to FIG. 6. In particular, the FHR data and the acoustic FHR data may be received as a result of an anomaly being detected in the FHR data, as described above. The FHR data may be transmitted in a data stream in accordance with the sUMF protocol. The acoustic FHR data may be transmitted in an audio stream in accordance with the sUMF protocol.

At 704, method 700 includes storing the FHR data and the acoustic FHR data in an FHR database (e.g., FHR database 364). By storing the FHR data and the acoustic FHR data in the FHR database, the FHR data and the acoustic FHR data may be accessed by a clinician, researcher, or a different health care professional at a later time.

At 706, method 700 includes notifying a clinician (e.g., a caregiver of the pregnant mother and fetus) of the detected anomaly, and transmitting the FHR data and the acoustic FHR data to a surveillance station to be viewed and/or listened to by the clinician. The surveillance station may be a non-limiting example of surveillance station 330 of FIG. 3. The FHR data and the acoustic FHR data may be transmitted to the surveillance station using the sUMF protocol.

At 708, method 700 optionally includes labeling the acoustic FHR data and storing the acoustic FHR data in a training database for training one or more ML models. The one or more ML models may be trained to detect anomalous patterns in the acoustic FHR data. For example, when the anomaly is detected by the one or more AI analytics models and/or anomaly detection model and recording of the acoustic FHR data is initiated, a description of the anomaly may be used to label the acoustic FHR data acquired from the recording. The labeled recording of the acoustic FHR data may then be used as ground truth when training an ML model to detect examples of the detected anomaly in new acoustic FHR data. The description of the anomaly may also be associated with the acoustic FHR data in the sUMF protocol when the acoustic FHR data is transmitted to the surveillance station.

At 710, method 700 includes determining whether a request is received to terminate transmitting the acoustic FHR data and/or delete the FHR data and/or the acoustic FHR data from the FHR database. For example, the clinician may review the FHR data and the acoustic FHR data at the surveillance station, and the clinician may determine a diagnosis of the fetus from the FHR data and the acoustic FHR data. The clinician may diagnose the fetus as healthy, and as a result, may determine that the FHR data and the acoustic FHR data is no longer desired to be stored, whereby the clinician may send a request to the analytics system to discontinue recording the acoustic FHR data. The clinician may also send a request to remove the FHR data and the acoustic FHR data from the FHR database. In some cases, the clinician may request that the non-acoustic FHR data be preserved in the FHR database, and/or that the non-acoustic FHR data continue to be acquired and sent to the surveillance station, and that the (larger) acoustic FHR data be removed from the FHR database. In other cases, the clinician may request that the acoustic FHR data not be transmitted to the analytics system, but may not request that the acoustic FHR data be removed from the FHR database.

If at 710 no request is received to delete the FHR data and/or the acoustic FHR data from the FHR database, method 700 proceeds back to 702, where method 700 includes continuing to receive the FHR data and the acoustic FHR data. Alternatively, if at 710 the request is received to delete the FHR data and/or the acoustic FHR data from the FHR database, method 700 proceeds to 712. At 712, method 700 includes deleting the FHR data and/or the acoustic FHR data from the FHR database, and method 700 ends.

Figure 8:
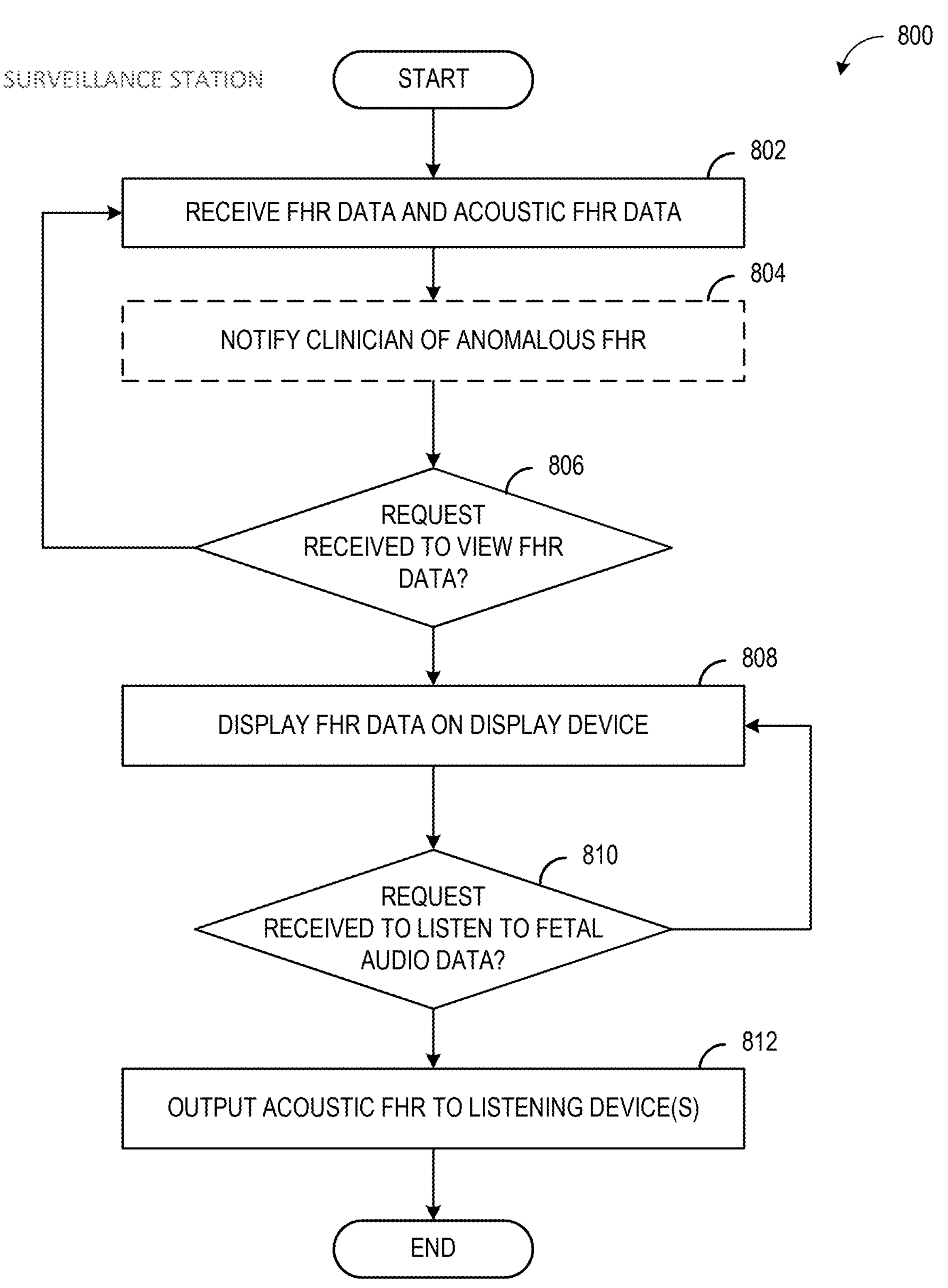
FIG. 8 is a flowchart illustrating an exemplary method for processing the fetal HR data including the acoustic fetal HR at the surveillance station.

Turning now to FIG. 8, an exemplary method 800 is shown for communicating FHR data and acoustic FHR data received from an analytics system (e.g., analytics system 352) to a clinician at a surveillance station (e.g., surveillance station 330). Operations of method 800 may be stored in non-transitory memory of the surveillance system (e.g., memory 333) and executed by a processor of the surveillance system (e.g., processor 331). In some embodiments, the FHR data and acoustic FHR data may be received from a fetal monitor (e.g., fetal monitor 302).

Method 800 begins at 802, where method 800 includes receiving the FHR data and the acoustic FHR data from the analytics system. The FHR data may be transmitted in a data stream in accordance with the sUMF protocol. The acoustic FHR data may be transmitted in an audio stream in accordance with the sUMF protocol.

At 804, method 800 optionally includes notifying the clinician of the anomalous FHR detected in the FHR data. In some cases, the clinician may be additionally or alternatively notified by the analytics system, as described above in reference to FIG. 7.

At 806, method 800 includes determining whether a request is received from a clinician to view the FHR data on a display device. The display device may be a display device of the surveillance station (e.g., display device 334), or a different display device communicatively couple to the surveillance station. In some examples, the display device may be a smart phone of the clinician.

In various embodiments, the request may be received when the clinician selects a control element, such as a real or virtual button, link, menu item, etc., in a graphical user interface (GUI) of the surveillance station (or a device communicatively coupled to the surveillance station. For example, a nurse may be working at the surveillance station, and a notification of the anomalous FHR detected in the FHR data may be displayed in the GUI on the display device of the surveillance station. The nurse may select the notification. When the notification is selected, the request may be received to view the FHR data on the display device.

If at 806 it is determined that no request is received, method 800 proceeds back to 802, where method 800 includes continuing to receive the FHR data and the acoustic FHR data at the surveillance station. Alternatively, if at 806 it is determined that the request is received, method 800 proceeds to 808.

At 808, method 800 includes displaying the FHR data on the display device. In various embodiments, the FHR data may be displayed as a continuous tracing of the FHR in a graph-like display, as shown in FIG. 4 and described above. Other characteristics, aspects, or information related to the continuous tracing may also be included in the sUMF protocol, and may be displayed on the display device concurrently with the continuous tracing. For example, a portion of the continuous tracing including the anomaly may be highlighted and/or labeled, links to additional information may be included, etc.

At 810, method 800 includes determining whether a request is received from a clinician to listen to the acoustic FHR data on a listening device (e.g., listening device 336). The listening device may include a speaker, headphones, earbuds, etc., connected to the surveillance station, or a different device (e.g., the smart phone) communicatively coupled to the surveillance station. As described above, the request may be received when the clinician selects a control element, such as a real or virtual button, link, menu item, etc., in the GUI of the surveillance station or a device communicatively coupled to the surveillance station.

Figure 9:
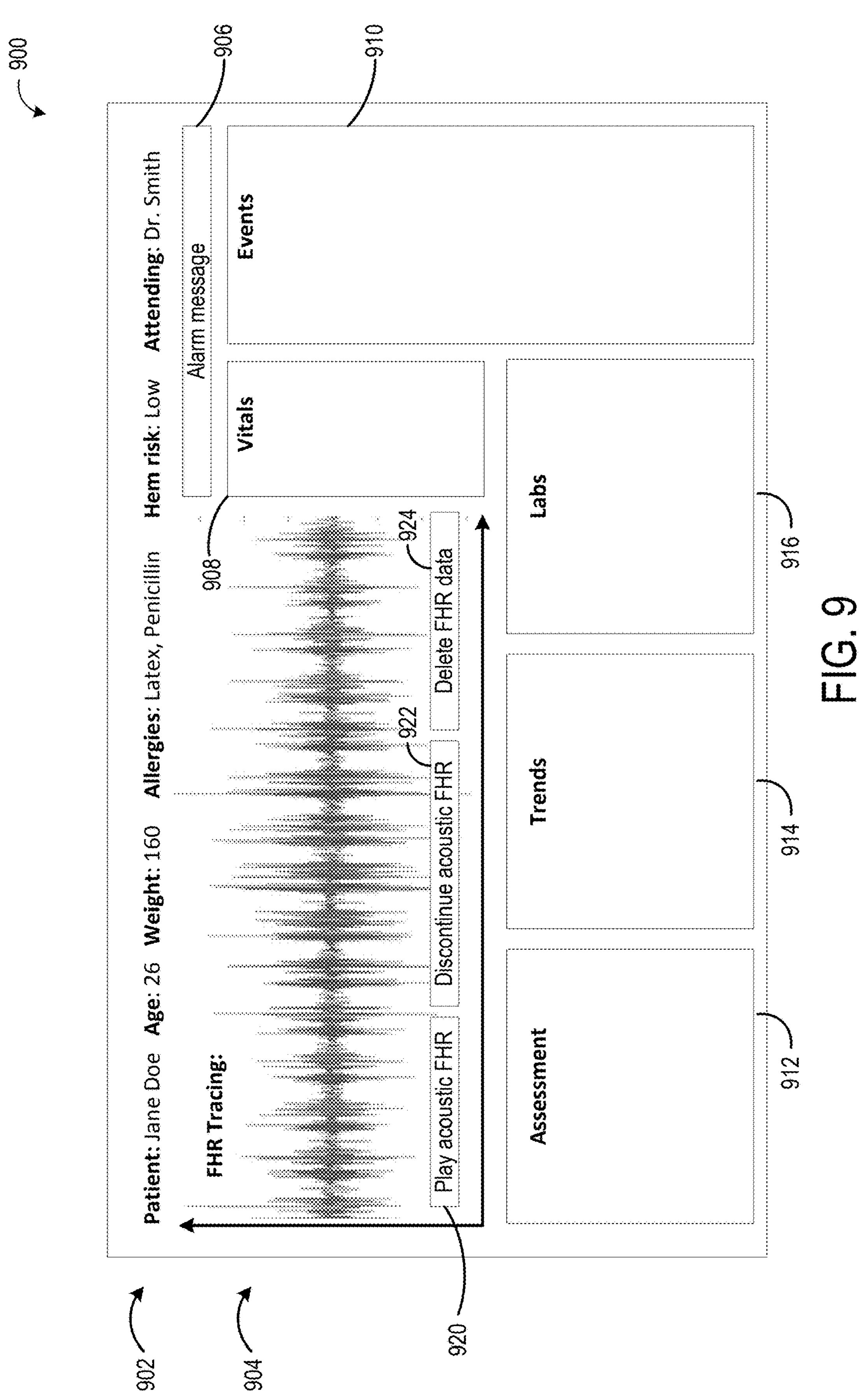
FIG. 9 is an exemplary graphical user interface (GUI) of a surveillance station.

Referring briefly to FIG. 9, an exemplary GUI 900 is shown of a surveillance system in which the FHR data may be displayed. GUI 900 is shown for illustration and not limitation; it should be appreciated that in other embodiments, GUI 900 may include different and/or additional elements, and/or depicted elements of GUI 900 may be arranged in a different layout. In the depicted embodiment, GUI 900 displays select patient information 902, such as a name of the mother, age, weight, allergies, risk of hemorrhage, and an attending physician of the mother. GUI 900 includes an FHR tracing 904, which indicates the FHR of the fetus in real time as the FHR data is received at the surveillance station. That is, FHR tracing 904 may be continuously updated, and may scroll across GUI 900 as new FHR data is received. GUI 900 includes an alarm message indicator 906, which may indicate whether one or more alerts or alarms have been triggered relating to the FHR data.

GUI 900 may include various data panels, such as a vitals data panel 908 that shows current vital signs of the mother; an events panel 910 that shows events detected in the FHR data, such as incidence of high blood pressure, low blood oxygen, etc.; an assessment data panel 912 that shows an assessment of a condition of the mother or fetus; a trends data panel 914 that shows trends in the FHR data; and a labs data panel 916 that shows recent lab results of the mother. GUI 900 also includes a button 920, which when selected by a user (e.g., the caregiver), may output the acoustic FHR to a listening device coupled to the surveillance station, as described above. GUI 900 further includes a button 922, which when selected may send a request to the analytics system to terminate acquiring the acoustic FHR data at the fetal monitor and transmitting the acoustic FHR to the analytics system, as described above in reference to FIG. 7. GUI 900 may also include a button 924, which when selected sends a request to the analytics system to delete the FHR data from the FHR database as described above in reference to FIG. 7. In this way, the user of GUI 900 may view current FHR data in a same display as other medical and physiological data of the mother and/or fetus, with the ability to additionally hear the acoustic FHR.

Returning to method 800, if at 810 it is determined that no request is received, method 800 proceeds back to 808, where method 800 includes continuing to display the FHR data on the display device. Alternatively, if at 810 it is determined that the request is received, method 800 proceeds to 812.

At 812, method 800 includes outputting the acoustic FHR data to the listening device. In some examples, the acoustic FHR data may be outputted to a plurality of listening devices. For example, a team of clinicians may be reviewing the FHR data of the fetus, and each clinician of the team of clinicians may have a different listening device coupled to the surveillance station. The acoustic FHR data may be outputted to each of the different listening devices of the team of clinicians. The acoustic FHR data may be outputted to each of the different listening devices simultaneously or concurrently with the display of the FHR data on the display device. In this way, the team of clinicians may review the acoustic FHR data together, in a collaborative manner. Method 800 ends.

As an example of how methods 500-800 may be performed in practice, a pregnant patient at a hospital may be monitored by a caregiver via a fetal monitoring system similar to fetal monitoring systems 12 and 300 of FIGS. 2 and 3, respectively. A FHR of the fetus may be monitored via an ultrasound system such as ultrasound system 100 and a tocodynameter. The caregiver may periodically review the FHR of a fetus of the patient on a display of a patient monitor (e.g., monitoring device 20 of FIG. 2). The caregiver may also leave the patient, and periodically review the FHR of the fetus on a tablet computing device of the caregiver remotely while working at a different location from the patient. The monitoring device may stream the FHR to an analytics system, using the sUMF protocol. The sUMF protocol may also encode other information of the patient, such as identifying information, medical history, lab results, identifying information of the caregiver, and/or other parameters (e.g., parameters 1006 of FIG. 10). At the analytics system, the FHR data may be analyzed using one or more AI analytics models. In particular, the FHR data may be inputted into an anomaly detection model continuously in real time. At a first time, the anomaly detection model may not detect an anomaly in the FHR. However, at a later time, the anomaly detection model may detect an anomalous pattern in the FHR data.

In response to the anomaly detection model detecting the anomalous pattern, the analytics system may send a request to the fetal monitor to acquire and transmit acoustic FHR data to the analytics system. The fetal monitor may acquire the acoustic FHR data from an electronic stethoscope or Doppler transducer positioned on an abdomen of the patient, for example, via an elastic strap as described in reference to FIG. 2. Because the sUMF protocol supports audio data streams, the fetal monitor may transmit the acoustic FHR data to the analytics system using the sUMF protocol, concurrently with the FHR data acquired via the ultrasound system and the toco.

When the FHR data and the acoustic FHR data is received at the analytics system, the analytics system may store either or both of the FHR data and the acoustic FHR data in the FHR database. The analytics system may retrieve contact information from the identifying information of the caregiver included in the sUMF protocol, and send a notification of the detected anomaly to the caregiver. The caregiver may receive the notification on their smart phone. The caregiver may log into a nearby surveillance station. After logging into the surveillance station, the caregiver may see the notification in a GUI of the surveillance station. The caregiver may select the notification to open the notification. When the notification is opened, the FHR data may be displayed in a window of the GUI. The FHR data may be displayed as a trace that continuously scrolls across the window in real time.

The caregiver may look for the anomaly in the trace displayed in the window. However, the caregiver may not clearly see the anomaly in the trace. For example, the anomaly may be intermittent, or subtle. The caregiver may select a control element of the GUI to listen to the FHR. When the caregiver selects the control, the acoustic FHR streamed from the fetal monitor to the analytics system and from the analytics system to the surveillance system may be outputted to a set of headphones coupled to the surveillance system. The caregiver may put on the headphones, and may listen to the acoustic FHR. While the caregiver is listening to the acoustic FHR, the caregiver may review other information of the fetus and/or pregnant mother, such as the medical history, lab results, etc. included in the streamed FHR data (e.g., stored using the sUMF protocol). After listening to the acoustic FHR via the headphones, the caregiver may hear the anomalous pattern in the FHR. As a result of hearing the anomalous pattern, the caregiver may diagnose the fetus with a condition.

In a first example, the condition may not be concerning to the caregiver. As a result of the condition not being concerning, the caregiver may select an element in the display to send a request to the analytics system to discontinue acquiring the acoustic FHR from the patient and transmitting the FHR to the analytics system. The caregiver may also send a request that the acoustic FHR data be removed from the FHR database, to save space in a memory of the analytics system.

In a second example, the condition may be concerning to the caregiver. As a result of the condition being concerning, the caregiver may wish to continue to record and monitor the FHR data and/or the acoustic FHR data of the fetus. Thus, the caregiver may not send the request to the analytics system to discontinue acquiring the acoustic FHR from the patient and transmitting the FHR to the analytics system, or that the acoustic FHR data be removed from the FHR database.

In this way, the caregiver may remotely monitor the FHR of the fetus from various locations within the hospital. However, unlike other conventional FHR monitoring systems that may transmit FHR data to a remote surveillance station, the disclosed FHR monitoring system leverages the capabilities of the sUMF protocol to additionally transmit the acoustic FHR data to the remote surveillance station, so that the caregiver can listen to the FHR in addition to or instead of viewing the continuous trace of the FHR displayed on the display device. Further, a plurality of caregivers may all listen to the FHR via individual listening devices, to collaborate in reviewing the FHR. As a result, remote physicians, clinicians, or command centers can ensure an intervention strategy for the fetus is appropriate, timely, and correlates to positive outcomes. The acoustic FHR data can also be used as input to train future AI models to provide comprehensive analytics, and/or to generate training materials for reviewing fetal strips. Because the sUMF protocol is used, the FHR data transmitted from the fetal monitor to the caregiver can be enriched with patient data (such as the acoustic FHR data) that is not supported by protocols used by conventional systems.

Additionally, an amount and/or size of the acoustic FHR data may be large, which may consume undesirable amounts of bandwidth during transmission and memory during storage. To address the problem of the size of the acoustic FHR data, the disclosed fetal monitoring system advantageously determines whether or not to acquire the acoustic FHR data based on an output of analytics performed at the analytics system. That is, the non-acoustic FHR data may be processed by various AI analytics models, which may detect anomalous patterns in the FHR data. The acoustic FHR data may be recorded and transmitted when an anomalous pattern is detected, and may not be recorded and transmitted when no anomalous pattern is detected. As a result, an amount of memory, processing resources, and bandwidth of the analytics system consumed by the acoustic FHR data may be reduced. By reducing the consumption of the memory, processing resources, and bandwidth, the disclosed fetal monitoring system may be feasible to operate using current computing environments, and may reduce a cost of operation of the fetal monitoring system.

The technical effect of transmitting an FHR of a fetus to an analytics system and/or a surveillance station using the sUMF protocol is that acoustic FHM data may be included with the FHM data, which may provide a greater amount of information that a clinician can review when monitoring the FHR. The technical effect of acquiring and transmitting the acoustic FHM data in response to an anomalous pattern being detected in the FHM data by an AI analytic model is that an amount of memory, processing resources, and bandwidth of the analytics system consumed by the acoustic FHR data may be reduced, lowering a cost of the fetal monitoring system and increasing an efficiency of the fetal monitoring system.

The disclosure also provides support for a fetal monitoring system, comprising: a fetal monitor including a processor and a non-transitory memory storing a set of instructions that when executed, cause the processor to: continuously acquire fetal heart rate (FHR) data of a fetus of a pregnant mother from one or more sensors arranged on an abdomen of the pregnant mother, process the FHR data received using one or more artificial intelligence (AI) models, and in response to the one or more AI models detecting an anomaly in the FHR data: initiate recording of acoustic FHR data of the fetus via the one or more sensors, store the FHR data and the acoustic FHR data in a database, display a continuous graphical tracing of the FHR data of the fetus on a display device, and output the acoustic FHR data to a listening device. In a first example of the system, the one or more sensors include an ultrasound transducer, a tocodynamometer transducer, an electronic stethoscope, and a Doppler transducer. In a second example of the system, optionally including the first example, the FHR data is processed using the one or more AI models by a cloud-based analytics system communicatively coupled to the fetal monitor, the graphical tracing of the FHR data is displayed on a display device of a surveillance station of a clinician communicatively coupled to the analytics system and the fetal monitor, and the acoustic FHR data is outputted to a listening device of the surveillance station. In a third example of the system, optionally including one or both of the first and second examples, the FHR data and the acoustic FHR data acquired at the fetal monitor are transmitted to the analytics system and the surveillance station using a universal messaging format (UMF) protocol. In a fourth example of the system, optionally including one or more or each of the first through third examples, further instructions are stored in the non-transitory memory that when executed, cause the processor to: in response to the one or more AI models detecting the anomaly in the FHR data: send a notification of the anomaly to the clinician, and display the continuous graphical tracing of the FHR data on the display device and output the acoustic FHR data to the listening device in response to the clinician opening the notification at the surveillance station. In a fifth example of the system, optionally including one or more or each of the first through fourth examples, further instructions are stored in the non-transitory memory that when executed, cause the processor to: in response to the one or more AI models not detecting the anomaly in the FHR data or receiving a request from the clinician: terminate recording of the acoustic FHR data, terminate storing the acoustic FHR data in the database, and not transmit the acoustic FHR data to the surveillance station. In a sixth example of the system, optionally including one or more or each of the first through fifth examples, the system further comprises: in response to the one or more AI models detecting the anomaly in the FHR data, output the acoustic FHR data simultaneously to a plurality of listening devices of one or more surveillance stations.

The disclosure also provides support for a method for a fetal monitoring system of a hospital, comprising: acquiring fetal heart rate (FHR) data of a fetus of a pregnant mother using a fetal monitor, transmitting the FHR data from the fetal monitor to an analytics system communicably coupled to the fetal monitoring system, processing the FHR data at the analytics system using one or more AI analytics models, in response to the one or more AI analytics models detecting an anomaly in the FHR data: sending a request from the analytics system to the fetal monitor to record acoustic FHR data of the fetus, and to transmit FHR data including the acoustic FHR data to the analytics system, sending the FHR data including the acoustic FHR data from the analytics system to a surveillance station of a clinician, displaying a continuous graphical tracing of the FHR data of the fetus on a display device of the surveillance station, and outputting the acoustic FHR data to a listening device of the surveillance station. In a first example of the method, the FHR data is time-series data continuously acquired and continuously transmitted to the analytics system in real time. In a second example of the method, optionally including the first example, the FHR data is ultrasound data acquired via an ultrasound transducer, and the acoustic FHR data is acquired via one of an electronic stethoscope and a Doppler transducer. In a third example of the method, optionally including one or both of the first and second examples, transmitting the FHR data including the acoustic FHR data to the analytics system further comprises transmitting the FHR data and the acoustic FHR data using a universal messaging format (UMF) protocol. In a fourth example of the method, optionally including one or more or each of the first through third examples, the analytics system is a cloud-based analytics system. In a fifth example of the method, optionally including one or more or each of the first through fourth examples, the one or more AI analytics models include a machine learning (ML) anomaly detection model trained to detect anomalous patterns in the FHR data. In a sixth example of the method, optionally including one or more or each of the first through fifth examples, the one or more AI analytics models include an AI model trained to classify the FHR data into one of a plurality of categories. In a seventh example of the method, optionally including one or more or each of the first through sixth examples, the method further comprises: in response to the one or more AI analytics models detecting the anomaly in the FHR data, storing the FHR data and the acoustic FHR data in a database of the analytics system. In a eighth example of the method, optionally including one or more or each of the first through seventh examples, the method further comprises: in response to the one or more AI analytics models not detecting the anomaly in the FHR data: not acquiring or terminating acquiring the acoustic FHR data at the fetal monitor, not storing the FHR data in the database, and not sending the FHR data from the analytics system to the surveillance station. In a ninth example of the method, optionally including one or more or each of the first through eighth examples, the method further comprises: in response to the one or more AI analytics models detecting the anomaly in the FHR data: sending a notification of the anomaly to a clinician, and displaying the continuous graphical tracing of the FHR data on the display device and outputting the acoustic FHR data to the listening device in response to the clinician opening the notification at the surveillance station. In a tenth example of the method, optionally including one or more or each of the first through ninth examples, the method further comprises: in response to detecting the anomaly in the FHR data: outputting the acoustic FHR data simultaneously to a plurality of listening devices of one or more surveillance stations.

The disclosure also provides support for a fetal monitoring system, comprising: a fetal monitor, a cloud-based analytics system, and a surveillance station, wherein: the fetal monitor includes a first processor and a first non-transitory memory storing a first set of instructions that when executed, cause the first processor to: continuously acquire fetal heart rate (FHR) data of a fetus of a pregnant mother from one or more sensors arranged on an abdomen of the pregnant mother, and in response to receiving a request from the cloud-based analytics system, initiate recording of acoustic FHR data of the fetus from the one or more sensors, and transmit the FHR data and the acoustic FHR data to the cloud-based analytics system, the analytics system includes a second processor and a second non-transitory memory storing a second set of instructions that when executed, cause the second processor to: process the FHR data received from the fetal monitor using one or more artificial intelligence (AI) models, in response to the one or more AI models detecting an anomaly in the FHR data: send a request to the fetal monitor to record and transmit the acoustic FHR data to the cloud-based analytics system, store the received FHR data and the acoustic FHR data in a database, notify a clinician of the anomaly, and transmit the received FHR data and the acoustic FHR data to the surveillance station, and the surveillance station includes a third processor and a third non-transitory memory storing a third set of instructions that when executed, cause the third processor to: display a continuous graphical tracing of the FHR data of the fetus on a display device, and output the acoustic FHR data to a listening device.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative and should not be construed to be limiting in any manner.

The invention claimed is:

1. A fetal monitoring system, comprising:
- a fetal monitor including a processor and a non-transitory memory storing a set of instructions that when executed, cause the processor to:
  - continuously acquire fetal heart rate (FHR) data of a fetus of a pregnant mother from one or more sensors arranged on an abdomen of the pregnant mother;
  - process the FHR data received using one or more artificial intelligence (AI) models;
  - in response to the one or more AI models detecting an anomaly in the FHR data:
    - initiate recording of acoustic FHR data of the fetus via the one or more sensors;
    - store the FHR data and the acoustic FHR data in a database;
    - display a continuous graphical tracing of the FHR data of the fetus on a display device; and
    - output the acoustic FHR data to a listening device; and
  - in response to the one or more AI models not detecting an anomaly in the FHR data, not recording the acoustic FHR data of the fetus, not storing the FHR data and the acoustic FHR data in a database, and not outputting the acoustic FHR data to a listening device.

2. The fetal monitoring system of claim 1, wherein the one or more sensors include an ultrasound transducer, a tocodynamometer transducer, an electronic stethoscope, and a Doppler transducer; and
- wherein the acoustic FHR data includes an audio stream that transmits recorded cardiograph data.

3. The fetal monitoring system of claim 1, wherein:
- the FHR data is processed using the one or more AI models by a cloud-based analytics system communicatively coupled to the fetal monitor;
- the graphical tracing of the FHR data is displayed on a display device of a surveillance station of a clinician communicatively coupled to the analytics system and the fetal monitor; and
- the acoustic FHR data is transmitted from the fetal monitor to a listening device of the surveillance station.

4. The fetal monitoring system of claim 3, wherein the FHR data and the acoustic FHR data acquired at the fetal monitor are transmitted to the analytics system and the surveillance station using the Sapphire over Unified Messaging Fabric (sUMF) protocol.

5. The fetal monitoring system of claim 3, wherein further instructions are stored in the non-transitory memory that when executed, cause the processor to:
- in response to the one or more AI models detecting the anomaly in the FHR data:
  - send a notification of the anomaly to the clinician; and
  - display the continuous graphical tracing of the FHR data on the display device and output the acoustic FHR data to the listening device in response to the clinician opening the notification at the surveillance station.

6. The fetal monitoring system of claim 3, wherein further instructions are stored in the non-transitory memory that when executed, cause the processor to:
- in response to the one or more AI models not detecting the anomaly in the FHR data or receiving a request from the clinician:
  - terminate recording of the acoustic FHR data;
  - terminate storing the acoustic FHR data in the database; and
  - not transmit the acoustic FHR data to the surveillance station.

7. The fetal monitoring system of claim 3, further comprising:
- in response to the one or more AI models detecting the anomaly in the FHR data, output the acoustic FHR data simultaneously to a plurality of listening devices of one or more surveillance stations.

8. A method for a fetal monitoring system of a hospital, comprising:
- acquiring fetal heart rate (FHR) data of a fetus of a pregnant mother using a fetal monitor;
- transmitting the FHR data from the fetal monitor to an analytics system communicably coupled to the fetal monitoring system;
- processing the FHR data at the analytics system using one or more AI analytics models;
- in response to the one or more AI analytics models detecting an anomaly in the FHR data:
  - sending a request from the analytics system to the fetal monitor to record acoustic FHR data of the fetus, and to transmit FHR data including the acoustic FHR data to the analytics system;
  - sending the FHR data including the acoustic FHR data from the analytics system to a surveillance station of a clinician;
  - displaying a continuous graphical tracing of the FHR data of the fetus on a display device of the surveillance station; and
  - outputting the acoustic FHR data to a listening device of the surveillance station;
- wherein transmitting the FHR data including the acoustic FHR data to the analytics system further comprises transmitting the FHR data and the acoustic FHR data using the Sapphire over Unified Messaging Fabric (sUMF) protocol.

9. The method of claim 8, wherein the FHR data is time-series data continuously acquired and continuously transmitted to the analytics system in real time, and wherein the acoustic FHR data includes an audio stream that transmits recorded cardiograph data.

10. The method of claim 9, wherein the FHR data is ultrasound data acquired via an ultrasound transducer, and the acoustic FHR data is acquired via one of an electronic stethoscope and a Doppler transducer.

11. The method of claim 8, wherein the analytics system is a cloud-based analytics system.

12. The method of claim 8, wherein the one or more AI analytics models include a machine learning (ML) anomaly detection model trained to detect anomalous patterns in the FHR data.

13. The method of claim 8, wherein the one or more AI analytics models include an AI model trained to classify the FHR data into one of a plurality of categories.

14. The method of claim 8, further comprising:

in response to the one or more AI analytics models detecting the anomaly in the FHR data, storing the FHR data and the acoustic FHR data in a database of the analytics system.

15. The method of claim 14, further comprising:

in response to the one or more AI analytics models not detecting the anomaly in the FHR data:

not acquiring or terminating acquiring the acoustic FHR data at the fetal monitor;

not storing the FHR data in the database; and not sending the FHR data from the analytics system to the surveillance station.

16. The method of claim 8, further comprising:

in response to the one or more AI analytics models detecting the anomaly in the FHR data:

sending a notification of the anomaly to a clinician; and displaying the continuous graphical tracing of the FHR data on the display device and outputting the acoustic FHR data to the listening device in response to the clinician opening the notification at the surveillance station.

17. The method of claim 8, further comprising:

in response to detecting the anomaly in the FHR data:

outputting the acoustic FHR data simultaneously to a plurality of listening devices of one or more surveillance stations.

18. A fetal monitoring system, comprising:

a fetal monitor, a cloud-based analytics system, and a surveillance station; wherein:

the fetal monitor includes a first processor and a first non-transitory memory storing a first set of instructions that when executed, cause the first processor to:

continuously acquire fetal heart rate (FHR) data of a fetus of a pregnant mother from one or more sensors arranged on an abdomen of the pregnant mother;

in response to receiving a request from the cloud-based analytics system, initiate recording of acoustic FHR data of the fetus from the one or more sensors, and transmit the FHR data and the acoustic FHR data to the cloud-based analytics system; and in response to not receiving the request from the cloud-based analytics system, not initiate recording of acoustic FHR data of the fetus from the one or more sensors, and not transmitting the FHR data and the acoustic FHR data to the cloud-based analytics system; and the analytics system includes a second processor and a second non-transitory memory storing a second set of instructions that when executed, cause the second processor to:

process the FHR data received from the fetal monitor using one or more artificial intelligence (AI) models;

in response to the one or more AI models detecting an anomaly in the FHR data:

send a request to the fetal monitor to record and transmit the acoustic FHR data to the cloud-based analytics system;

store the received FHR data and the acoustic FHR data in a database;

notify a clinician of the anomaly; and transmit the received FHR data and the acoustic FHR data to the surveillance station; and in response to the one or more AI models not detecting the anomaly in the FHR data, not sending the request to the fetal monitor to record and transmit the acoustic FHR data to the cloud-based analytics system, not storing the received FHR data and the acoustic FHR data in a database, and not transmitting the acoustic FHR data to the surveillance station; and the surveillance station includes a third processor and a third non-transitory memory storing a third set of instructions that when executed, cause the third processor to:

display a continuous graphical tracing of the FHR data of the fetus on a display device; and output the acoustic FHR data to a listening device.

19. The fetal monitoring system of claim 18, wherein the FHR data and the acoustic FHR data acquired at the fetal monitor are transmitted to the cloud-based analytics system using the Sapphire over Unified Messaging Fabric (sUMF) protocol.

* * * * *